United States Patent [19]
Knuth et al.

[11] Patent Number: 5,989,554
[45] Date of Patent: Nov. 23, 1999

[54] HIGH LEVEL EXPRESSION AND FACILE PURIFICATION OF PROTEINS, PEPTIDES AND CONJUGATES FOR IMMUNIZATION, PURIFICATION AND DETECTION APPLICATIONS

[75] Inventors: Mark W. Knuth, Waunakee; Mary Haak-Frendscho, Madison; John W. Shultz, Verona; Scott A. Lesley, Oregon; Catherine E. Villars, McFarland, all of Wis.

[73] Assignee: Promega Corporation, Madison, Wis.

[21] Appl. No.: 09/174,060

[22] Filed: Oct. 16, 1998

Related U.S. Application Data

[62] Division of application No. 08/338,382, Nov. 10, 1994.
[51] Int. Cl.⁶ .......................... A61K 39/00; A61K 39/385
[52] U.S. Cl. ..................... 424/192.1; 424/184.1; 424/185.1; 424/186.1; 424/193.1
[58] Field of Search ............................. 424/184.1, 185.1, 424/186.1, 192.1, 193.1

[56] References Cited

U.S. PATENT DOCUMENTS

| | | | |
|---|---|---|---|
| 4,512,922 | 4/1985 | Jones et al. | 530/408 |
| 4,743,679 | 5/1988 | Cohen et al. | 530/350 |
| 4,952,496 | 8/1990 | Studier et al. | 435/91.41 |
| 5,008,373 | 4/1991 | Kingsman et al. | 530/350 |
| 5,043,158 | 8/1991 | Sleytr et al. | 424/197.11 |
| 5,302,526 | 4/1994 | Keck et al. | 435/252.33 |
| 5,322,769 | 6/1994 | Bolling et al. | 435/5 |
| 5,322,930 | 6/1994 | Tarnowski et al. | 530/350 |

FOREIGN PATENT DOCUMENTS

WO 92/02550 2/1992 WIPO .

OTHER PUBLICATIONS

Duong, Le T.; Caulfield, Michael P., and Rosenblatt, Michael, Synthetic Signal Peptide and Analogs Display Different Activities in Mammalian and Plant in Vitro Secretion Systems, *The Journal of Biological Chemistry* (May 5, 1982), Baltimore, MD, USA, v262, No. 13, pp. 6328–6333.
Lin, Shu–Wha; Dunn, John J.; Studier, F. William; and Stafford, Darrel W., Expression of Human Factor IX and Its Subfragments in *Escherichia coli* and Generation of Antibodies to the Subfragments, *Biochemistry* (1987), v26, pp. 5267–5274.
Ngsee, Johnny K.; Hansen, William; Walter, Peter; and Smith, Michael, Cassette Mutagenic Analysis of the Yeast Invertase Signal Peptide: Effects on Protein Translocation, *Molecular and Cellular Biology* (Aug. 9, 1989), Washington, DC, US, v9, No. 8, pp. 3400–3410.
Randall, L.L. and Hardy, S.J.S., Unity in Function in the Absence of Consensus in Sequence: Role of Leader Peptides in Export, *Science* (Mar. 3, 1989), Washington, D.C., USA, v243, pp. 1156–1159.
Tamamoto, Yoshio; Taniyama, Yoshio; Kikuchi, Masakazu; and Ikehara, Morio, Engineering of the Hydrophobic Segment of the SignalSequence For Efficient Secretion of Human Lysozyme by Saccharomyces cerevisiae; *Biochemical and Biophysical Research Communications* (Dec. 16, 1987), Duluth, MN, USA, v149, No. 2, pp. 431–436.
Bolivar et al, (1977), *Gene* 2:95.
Clewell, D. R. et al, (1969), *Proc Nat Acad Sci USA* 62: 1159.
Cohen, S.N., (1972), *Proc Nat Acad Sci USA* 69: 2110.
*Current Protocols in Molecular Biology* (1994); chapter 16.
Klein, J., (1990) *Immunology*, Blackwell Scientific Publications, Inc. Massachusetts, 269–293.
Kohler & Milstein, (1975), *Nature*, 256: 495.
Lin, S. et al., (1987), *Biochemistry*, 26: 5267–5274.
Sano, C. et al., (1992), *Science* 258: 120–122.
Smith, A. J. et al., (1992), *Techniques in Protein Chemistry III*, 219–229.
Studier F. W., et al, (1990), *Meth. Enzym.* 185: 60–89.
Tae H. J., et al., (1983), *Methods in Enzymology* (Chapter 51), Academic Press, Inc., 91: 580–609.
Hey et al. (1994) A two fusion partner system for raising antibodies against small immunogens expressed in bacteria. Journal of Immunological Methods 173(2): 149–156, Aug. 1994.

*Primary Examiner*—Robert A. Wax
*Assistant Examiner*—Einar Stole
*Attorney, Agent, or Firm*—Grady J. Frenchick; Karen B. King; Michael Best & Friedrich LLP

[57] ABSTRACT

A process for producing and purifying peptides and for producing peptide/protein antigens for antibody production is described. The process utilizes fusion proteins and specifically fusion proteins in which the fusion protein carrier segment includes an amino acid sequence at least about 65 amino acids long and in which the amino acid sequence does not contain negative or positive charged side chains of amino acids.

5 Claims, 18 Drawing Sheets

Met Ala Ser Val Thr Gly Gly Gln Gln Val Gly Thr Asn Gln Gly
 1           5                  10                  15

His Gly Val Val Ala Ala Gly Thr Gly Leu Ala Leu Phe Leu His
             20                  25                  30

Val Phe Gly Gly Thr Val Leu Thr Ala Phe Ala Gln His Thr Ser
             35                  40                  45

Val Thr Thr Ser His Val Val His Ser Ile Ser Ser Ala Asn Ser
             50                  55                  60

Ala Gln Phe Pro Val Leu Gly His Thr Gln Ala Ala Tyr Leu Ala
             65                  70                  75

Pro Gly Asn Gln

FIG. 1

Leu Gly Ile Pro Thr Ser Arg Asp Pro Gly Pro Leu Asp Ala Ala
 1           5               10              15

Ala Cys Ile Ser Leu Ser Ile Leu
            20

FIG. 2

```
Met Ala Ser Val Thr Gly Gly Gln Gln Val Gly Thr Asn Gln Gly
 1               5                   10                  15

His Gly Val Val Ala Ala Gly Thr Gly Leu Ala Leu Phe Leu His
                20                  25                  30

Val Phe Gly Gly Thr Val Leu Thr Ala Phe Ala Gln His Thr Ser
                35                  40                  45

Val Thr Thr Ser His Val Val His Ser Ile Ser Ser Ala Asn Ser
                50                  55                  60

Ala Gln Phe Pro Val Leu Gly His Thr Gln Ala Ala Tyr Leu Ala
                65                  70                  75

Pro Gly Asn Gln Leu Gly Ile Pro Thr Ser Arg Asp Pro Gly Pro
                80                  85                  90

Leu Asp Ala Ala Ala Cys Ile Ser Leu Ser Ile Leu
                95                  100
```

FIG. 3

HIGH LEVEL EXPRESSION AND FACILE PURIFICATION OF PROTEINS, PEPTIDES AND CONJUGATES FOR IMMUNIZATION, PURIFICATION AND DETECTION APPLICATIONS

This application is a division of application Ser. No. 08/338,382, filed Nov. 10, 1994.

FIELD OF THE INVENTION

Generally, the present invention is directed to the field of recombinant DNA technology. More particularly the present invention is directed to a process for producing and purifying peptides for multiple uses and producing antigens for antibody production. The present invention also is directed to the high level expression of small to medium sized ligands utilizing recombinant DNA technology. Specifically, the present invention is directed to an antigen production system utilizing fusion proteins. The present invention also is directed to an efficient method for presenting an antigen to an animal or human immune system.

CITED REFERENCES

A full bibliographic citation of the references cited in this application can be found in the section preceding the claims.

DESCRIPTION OF THE PRIOR ART

The present invention generally relates to markets where the detection or purification of molecules is involved. Representative markets include in vitro and in vivo diagnostics, research products, clinical products, clinical research products, pharmaceuticals and many industrial markets. These markets necessarily require a tight binding and specific affinity ligand that recognizes the biomolecule of interest. Given the importance of affinity recognition for proteins in a wide variety of markets, new methods for generating "immunoaffinity" or "macromolecular recognition" ligands using DNA technology are sought.

The production of proteins and peptides by recombinant DNA technology is now relatively common. Recombinant expression of peptides often is accomplished by inserting a DNA sequence encoding the desired peptide into an expression vector. The expression vector generally contains regulatory sequences which are recognized by the host cell, and which provide for transcription and translation of the inserted DNA to produce the peptide. The expression vector is inserted into a suitable whole cell, typically a procaryotic organism, in culture. The expression vector also usually includes a selectable marker, so that one may identify those cells which have been transformed successfully and carry the vector, and separate them from those which do not carry the vector.

Peptides may be expressed either directly or in the form of a fusion protein. Direct expression involves the production of the desired protein or peptide without modification. However, this form of expression often results in low yields and degradation of the product, particularly with small peptides.

One method commonly employed to increase the yield of the desired peptide is to express it as part of a fusion protein. In this approach, a leader protein, hereafter referred to as a carrier segment, is selected which is expressed easily in the host of choice. Often this protein is native to the host, as in the case of β-galactosidase. An expression vector encoding the carrier segment then is modified using standard molecular cloning techniques to express the desired peptide linked to the carrier segment. Most often, the peptide is linked to the carboxy terminus of the carrier segment but, in principle, it could be linked anywhere through a normal peptide linkage.

The expression of the peptide as a fusion protein with the carrier segment may imbue it with new, favorable properties. For instance, the fusion protein can be injected into a host animal to create antibodies to the peptide or to produce a vaccine. The technology of using fusion proteins as antigens is well-known to the art (Current Protocols, 1994, Chapter 16). other favorable properties of the fusion protein may include ease of purification, the ability to be immobilized on surfaces, and the creation of bifunctional molecules (Santo, C. et al. 1992).

Although peptides with desired additional properties are commonly produced by the use of fusion proteins, it is also common to produce a peptide separately through chemical synthesis. The peptide then can be covalently coupled to purified carrier segments using chemical crosslinking agents. The resultant carrier protein conjugate can be used in many of the same applications as the fusion protein described above.

For example, peptides are sometimes covalently coupled to keyhole limpet hemocyanin for immunizations or to alkaline phosphatase for use as a detection reagent. In the case of the fusion protein, the only molecules which can be linked to the carrier segment are peptides, and the linkage must be through the normal polypeptide backbone.

When the second molecule is coupled chemically to the carrier segment after expression, the nature of both the second molecules, called ligands, and of the chemical linkages to the carrier segment is much broader. Any ligand and crosslinker which is chemically allowed can be contemplated.

In some cases, covalent association of the ligand (peptide, hapten, or other) with the carrier segment is not required to be effective. The two molecules associate with each other by any number of means. In this case, the mixture of the two is called a carrier protein complex.

The following paragraphs illustrate some uses of prior art fusion proteins. For example, U.S. Pat. No. 4,743,679 to Cohen et al. discloses the expression of epidermal growth factor (EGF) as a fusion protein with a leader sequence of up to 200 amino acids (preferably up to 75). The fusion protein is expressed in bacteria as an insoluble inclusion body.

U.S. Pat. No. 5,302,526 to Keck et al. is directed to recombinant DNA encoding amphophilic leader sequences (carrier segments) for the production and purification of fusion proteins. The polypeptide comprises an amphophilic helix designed to have hydrophilic charged amino acid residues on one side and nonpolar amino acid residues on the other side of the helix. When a gene encoding a protein of interest is attached to the helix, an inclusion body is formed. The inclusion bodies may be collected and purified.

U.S. Pat. No. 5,322,930 to Tarnowski et al. describes a method for expressing proteins as fusion proteins by using the portion of human pro-atrial natriuretic peptide (proATP) as the carrier for a heterologous peptide, wherein each of the Glu residues normally present in the proATP protein portion is altered to Gln.

U.S. Pat. No. 5,008,373 to Kingsman et al. describes a fusion protein system useful in vaccines or in diagnostic or purification applications. The fusion protein includes a first amino acid sequence derived from a retrotransposon or an RNA retrovirus encoded for by a yeast TYA gene sequence.

The second amino acid sequence is a biologically active amino acid sequence, acting as the antigen.

U.S. Pat. No. 5,322,769 to Bolling, et al. is directed to a method for using CKS fusion proteins in assays.

Lin et al. (1987) disclose the use as an antigen of a fusion protein containing a carrier segment consisting of the gene 10 molecule of phage T7.

A major problem with prior art carrier segments is that the carrier segments also are known to be antiqenic; that is, antibodies are produced in response to the carrier segment. Thus, there is a competition between the production of antibodies to the desired ligand and the production of antibodies to the carrier segment which may result in a lower production of antibodies with specificity for the target segment. Since the immune system usually reacts to surface exposed peptide segments which are often charged, it is likely that the existence of charged residues on the carrier segment exacerbates such pr6biems with antigenicity.

Another problem with prior art carrier segments is that they often require the use of adjuvants. Adjuvants serve a variety of purposes (Klein, 1990). Adjuvants trap the antigen by causing the formation of an emulsion, precipitate or small vesicles at the injection site from which the antigen is released slowly over a prolonged period. The clearance of the antigen is thus delayed and the organism's exposure to the antigen is lengthened. Adjuvants also stimulate the nonspecific migration of cells to the site of antigen injection and increase the probability of interaction of the antigen with cells of the immune system. Further, adjuvants increase antigen dispersion in the recipient's body by continually delivering the antigen in small amounts from the injection site to the regional lymph nodes or spleen. Some adjuvants also have a mitogenic effect and so stimulate the proliferation of lymphocytes nonspecifically. Some adjuvants also help to stimulate lymphocytes by activating adenylate cyclase and other chemical messengers. Adjuvants may increase the probability of contact among T- and B-cells, macrophages, and antigens through the activation of lymphocyte-trapping mechanisms. The main problem with adjuvants is that some of the most effective ones tend to be toxic to and/or cause lesions in the host organism. They also can be difficult to handle.

SUMMARY OF THE INVENTION

The present invention is directed to a fusion protein carrier segment comprising a non-naturally occurring, hydrophobic, sparingly soluble amino acid sequence.

The present invention is also directed to a substantially nonantigenic fusion protein carrier segment comprising a non-naturally occurring, hydrophobic, sparingly soluble amino acid sequence having a length at least about 65 amino acids long, wherein the carrier segment comprises no more than approximately 5% of the following amino acids arginine, lysine, aspartic acid, glutamic acid, cysteine, tryptophan and methionine.

The present invention further is directed to a carrier protein conjugate comprising a first amino acid sequence, wherein the first amino acid sequence is at least about 65 amino acids long and the first amino acid sequence lacks at least two of the following amino acids selected from the group consisting of the following negatively or positively charged side chains of amino acids: arginine, lysine, aspartic acid, glutamic acid; or uncharged side chains of the following amino acids: cysteine, tryptophan and methionine (with the exception of methionine at the amino terminal site); and a ligand fused to the first amino acid sequence.

Further, the present invention is directed to an amino acid sequence as illustrated in FIG. 1 [SEQ. ID. 1] or to an amino acid sequence as illustrated in FIG. 3 [SEQ. ID. 2].

The present invention also is directed to a non-naturally occurring fusion compound comprising an amino acid sequence as illustrated in FIG. 1 [SEQ. ID. 1] linked to a ligand.

The present invention also is directed to an expression vector comprising an amino acid sequence in a single reading frame with a coding sequence for an antigen, wherein the expression vector expresses a particle-forming fusion protein encoded by the amino acid sequence and a ligand, wherein the amino acid sequence is a non-naturally occurring, hydrophobic, sparingly soluble amino acid sequence wherein the amino acid sequence lacks at least two of the following amino acids selected from the group consisting of the following negatively or positively charged side chains of amino acids: arginine, lysine, aspartic acid, glutamic acid; or uncharged side chains of the following amino acids: cysteine, tryptophan and methionine (with the exception of methionine at the amino terminal site).

The present invention further is directed to an adjuvant for administering a high molecular weight protein to a host animal, the adjuvant comprising a non-naturally occurring, hydrophobic, sparingly soluble amino acid sequence.

The present invention also is directed to a process for producing an antibody to a ligand comprising: a) fusing a carrier segment comprising a non-naturally occurring hydrophobic sparingly soluble amino acid sequence to the ligand to form a fusion protein or carrier protein conjugate or carrier protein complex; b) presenting the antigen by in vivo or in vitro means; and c) producing the antibody to the ligand by in vivo or in vitro means.

The present invention also is directed to an assay for determining the concentration of an anti-antigen antibody in a test sample, wherein (a) at least a carrier protein conjugate is attached to a solid phase as capture reagent and is contacted with the test sample for a time and under conditions suitable for antigen/antibody of complexes to occur, and (b) an indicator reagent comprised of a signal generating compound and a specific binding member for the analyte is contacted with the complexes for time sufficient for a reaction to occur, wherein the signal generated is an indication of the presence of the anti-analyte antibody in the test sample. The improvement comprises attaching a fusion protein carrier segment comprising a non-naturally occurring hydrophobic sparingly soluble amino acid sequence to the solid phase as the capture reagent.

The present invention is further directed to a process for vaccinating a host vertebrate animal with an immunogen, comprising: (a) preparing an immunogen comprising a substantially nonantigenic fusion protein carrier segment containing a non-naturally occurring, hydrophobic, sparingly soluble amino acid sequence having a length at least about 65 amino acids long wherein the amino acid sequence lacks at least two of the following amino acids selected from the group consisting of the following negatively or positively charged side chains of amino acids: arginine, lysine, aspartic acid, glutamic acid; or uncharged side chains of the following amino acids: cysteine, tryptophan and methionine (with the exception of methionine at the amino terminal site); and (b) administering the carrier protein conjugate to the host vertebrate animal.

The present invention also is directed to a process for vaccinating a host vertebrate animal with an immunogen, comprising: (a) forming an immunogen comprising a non-naturally occurring carrier protein conjugate containing an amino acid sequence as illustrated in FIG. 1 [SEQ. ID. 1] and a ligand fused to the amino acid sequence; and (b) administering the carrier protein conjugate to the host vertebrate animal.

Further, the present invention is directed to a process for immunopurifying antibodies from a pool of antibody material, comprising: (a) forming a substantially nonantigenic fusion protein carrier segment containing a non-naturally occurring, hydrophobic, sparingly soluble amino acid sequence having a length at least about 65 amino acids long wherein the amino acid sequence lacks at least two of the following amino acids selected from the group consisting of the following negatively or positively charged side chains of amino acids: arginine, lysine, aspartic acid, glutamic acid; or uncharged side chains of the following amino acids: cysteine, tryptophan and methionine (with the exception of methionine at the amino terminal site); (b) incubating the antibody material with the carrier protein conjugate under binding conditions to bind the antibody material to the carrier protein conjugate to form an antibody/conjugate complex; (c) separating out the antibody/conjugate complex; (d) dissociating the antibody from the antibody/conjugate complex; and (e) separating the antibody from the antibody/conjugate complex.

Further, the present invention is directed to a process for producing peptides, comprising: (a) incubating a fusion protein containing a fusion protein carrier segment comprising a non-naturally occurring hydrophobic sparingly soluble amino acid sequence, wherein the amino acid sequence lacks at least two of the following amino acids selected from the group consisting of the following negatively or positively charged side chains of amino acids: arginine, lysine, aspartic acid, glutamic acid; or uncharged side chains of the following amino acids: cysteine, tryptophan and methionine (with the exception of methionine at the amino terminal site), under conditions where the peptide bonds on the fusion protein are cleaved; and (b) separating out the desired peptides.

Further, the present invention is directed to a protease inhibitor comprising a fusion protein containing a fusion protein carrier segment comprising a non-naturally occurring hydrophobic sparingly soluble amino acid sequence and a cleavage site for a protease, wherein the fusion protein is isolated and used as a competitive inhibitory substrate.

Further still, the present invention is directed to a solid support having absorbed thereon a carrier protein conjugate comprising: (a) a first amino acid carrier sequence, wherein the first amino acid sequence is at least about 65 amino acids long and the amino acid sequence lacks at least two of the following amino acids selected from the group consisting of the following negatively or positively charged side chains of amino acids: arginine, lysine, aspartic acid, glutamic acid; or uncharged side chains of the following amino acids: cysteine, tryptophan and methionine (with the exception of methionine at the amino terminal site); and (b) a ligand fused to the first amino acid carrier sequence.

The present invention also is directed to an assay for determining the concentration of an enzyme in a test sample, wherein (a) at least a carrier protein conjugate containing a ligand upon which the enzyme can act is attached to a solid phase and is contacted with the test sample for a time and under conditions suitable for the enzyme to act upon the substrate, and (b) indicator reagents capable of generating a signal change in response to the enzyme-catalyzed modification of the immobilized substrate is contacted with the complexes for time sufficient for a reaction to occur, wherein the signal generated is an indication of the presence of the enzyme in the test sample. The improvement comprises attaching a recombinant fusion protein carrier segment comprising a non-naturally occurring hydrophobic sparingly soluble amino acid sequence to the solid phase as the capture reagent.

The present invention also is directed to a test kit for use in detecting the presence of anti-antigen antibodies in a test sample, which test kit contains a container containing at least one protein specific for the anti-antigen antibody and, wherein the improvement comprises a container containing a non-naturally occurring hydrophobic sparingly soluble amino acid sequence, which is specific for the anti-antigen antibody.

The present invention also is directed to an immunoassay kit for detecting a specific antigen, comprising in separate containers:

a. a solid support having bound thereto one or more antibodies produced according to the process described above that will specifically react with a desired antigen;

b. a buffer to remove unbound proteins;
c. solutions for detection of bound analyte; and
d. instructions for use.

The advantages of the present invention are specifically directed to the novel carrier segment. Some of the advantages of the carrier segment are as follows:

Low Antigenicity: One of the primary goals of the present invention is to make antibodies to a ligand. In order to have the best opportunity to make the antibodies to the ligand, the carrier segment portion of the fusion protein must be relatively nonantigenic to the animal. Typically, the immune system in a host body will target foreign materials, i.e., antigens presented to the system. When an antigen such as a fusion protein enters the body, the immune system will seek out the most antigenic moiety to attack. If the carrier segment happens to contain the most notable antigen, the immune system will preferentially target the carrier segment and have little response to the target ligand segment of choice. This is often the case primarily because the carrier sent tends to be the larger segment, usually 300 or more amino acids. In naturally occurring proteins used as carrier segments, there are also a large number of charged amino acids.

Charged amino acid sequences are more likely to be surface-exposed and antigenic than are hydrophobic amino acid sequences. Thus, the carrier segment has more potential epitopes, and consists of residues which frequently are more easily recognized as foreign or dangerous by the immune system. By making the carrier segment small and very low in antigenicity, the immune system will be more likely to attack the ligand and produce antibodies to the ligand.

For the purposes of the present invention, low antigenicity is defined as failure of the carrier segment to induce formation of greater than 50% of the specific antibody generated in response to three or more injections into chickens, mice and rabbits of a fusion protein consisting of the carrier segment fused to a ligand having the sequence: $H_2N$-Lys Met Ala Glu Asp Asp Pro Tyr Leu Gly Arg Pro Glu Gln Met [SEO. ID 4]

One way of reducing the antigenicity of the carrier segment is to reduce its size. This allows the attached ligand to comprise a significantly greater fraction of the total fusion protein. Typically, the carrier segment contains between approximately 200 and 500 amino acids in length. However, by reducing the length of the segment to an amino acid length of approximately 100 or fewer amino acids and removing many charged amino acids, the carrier segment is less effectively displayed to the immune response in the host organism. The carrier segment should be at least 65 amino acids long, and rably 100 amino acids long. At the very least, the length of the carrier peptide should be sufficiently long to allow effective expression within the procaryotic host expression organism.

Low Solubility: A major advantage of the present carrier segment is that it is sparingly or slowly soluble. This results in an advantage for rapid purification since injection quality immunogen containing low levels of pyrogen can be prepared using simple washes as opposed to conventional methods such as chromatography, thus resulting in savings in both time and equipment. Additionally, the sequestration of the peptides in inclusion bodies when expressed may protect labile sequences from proteolytic attack.

No Need for Adjuvants: An additional advantage of the carrier segment is that it may act as its own adjuvant as well as a conventional carrier protein due to various properties of the carrier segment and of conjugates containing the segment, including low solubility and mitogenic effects.

A typical way researchers currently prepare antigens for production of antibodies is to chemically synthesize the ligand or peptide using techniques known to the art, and then to chemically crosslink it to a larger protein, known as a carrier protein. The function of the carrier protein is to elicit T-cell help. T-cell help is important in producing an effective antibody response within an animal. However, many ligands and peptides are too small to both present the desired antigenic site and to include a segment which allows the material to elicit T-cell help. Certain proteins, such as keyhole limpet hemocyanin, are known to the art to contain effective sites for eliciting T-cell help, and are thus often coupled to small ligands for this purpose. Unfortunately, as discussed previously, many of these also are antigenic and can dominate the antibody response. The carrier segment described elicits the necessary T-cell help without dominating the antibody responses and thus is a superior carrier protein.

A typical way researchers currently prepare a dosage of the antigen for injection for the production of antibodies is to formulate it in any number of suspension, precipitate or emulsion forms, called adjuvants. Adjuvants can augment the immune response as the result of the combined effect of several factors. If the antigen were injected into the host animal as is, it would be in a soluble form and would be quickly dispersed from the site of injection and cleared from the body. Since the immune system needs time to recruit immune cells to the site of injection and to mount a response, the quick dispersal and clearance of antigen is detrimental to the immune response. Formulation of the antigen so that it is trapped at the site of injection is an effort to keep the antigen localized long enough for the immune system to locate it and mount a response. In most cases, the antigen is not trapped long enough at the site to elicit a robust immune response, so multiple injections over a period of several weeks are required. Additionally, recruitment of immune cells to the site of injection usually requires some local nonspecific inflammation. For this reason, some adjuvant formulations also contain an irritant for this purpose. Adjuvants also may trap the recruited immune cells, thereby enhancing the interactions of the immune cells. Finally, adjuvants may stimulate proliferation of the immune cells.

The low solubility of the carrier segment and of conjugates containing it creates conditions at the injection site that are sufficient for mounting an immune response; namely, that some sort of nonspecific inflammatory response is created that recruits immune cells to the location, that antigen is sequestered at the site long enough for an immune response to be mounted, that interactions between the immune cells may be potentiated, and that immune cell proliferation is stimulated. If the solubility were too low, or if the antigen were not accessible to the immune system, no response would be achieved; thus, the solubility of the carrier segment is thought to be in an optimal range which balances the need for sequestration against the requirement for slight solubility and effective antigen display. Thus, the carrier segment has been designed to provide all functions required for eliciting an immune response; recruitment of immune cells to the injection site, sequestration of antigen at the site, eliciting T-cell help without dominating the antibody response, and effective antigen display to the immune system. The advantages of this system over prior art is that it eliminates the need for a step involving coupling to a carrier protein, and a step involving formulation in an adjuvant. Additionally, a single injection of antigen is sufficient to elicit an ample immune response.

Most adjuvants induce the formation of granulomas in animals and humans. For this reason, most adjuvants are not allowed for use in humans although they are allowed for use in animals (Klein, 1990). Therefore, a system which does not require the use of adjuvants is not only more humane, but may have significant benefits specifically in the field of vaccine development.

Using the carrier segment described, antibody isotype response may be able to be altered. Different isotypes or classes of antibody heavy chains are known to have unequal effector functions, such as the capacity to fix complement, and unequal capacity to bind available affinity resins, such as Protein A. Thus, antibodies with the same antigen specificity but of a different isotype have disparate effector functions and resin-binding affinities. The system of the present invention induces different antibody isotype profiles in response to different concentrations of the antigen. This suggests that a system may be developed which will allow the regulation of the predominant isotype or class of the antibodies which are made using this technology.

Excellent Expression: The property of excellent expression simplifies the production of a fusion protein by allowing small fermentations to be performed for the isolation of sufficient antigens for immunizations as well as subsequent uses such as validation assays and affinity purification regimens. It is logical to assume that enough of the fusion protein must be made in order for it to be injected into the host animal for antibody production. Usually, research requires the injection of more than one host animal. The carrier segment of the present invention is advantageous in that it is able to be expressed at a very high rate, e.g., $\geq 5$ mg/l in standard culture medium, in bacteria. Another advantage is that it allows the accumulation of the peptide without rapid degradation, thus allowing intact fusion proteins to be isolated.

Works with a Variety of Target Ligands: Another advantage of the carrier segment of the present invention is that it is relatively nonspecific in terms of attaching to target ligands. Therefore, virtually any type of ligand can be fused to the nonantigenic, sparingly soluble carrier segment to produce a useful immunogen in which the carrier segment is nonantigenic and the desired peptide is selectively displayed to the immune system.

Broad Utility as an Antigen: Another advantage of the present invention is that the fusion protein created by the carrier segment of the present invention creates enhanced antigenic responses in most antibody producing species. Typical species include vertebrates such as the mouse, rat, rabbit, chicken, goat, sheep, donkey, horse and human. The fusion protein has been shown to be effective using a variety of routes of injection as discussed infra.

Yield of Specific Antibodies Can be High: Another advantage of the present invention is that the ratio of specific antibodies to the ligand of interest compared to those antibodies directed against the carrier segment of the fusion conjugate is high. Typical carriers, such as KLH or BSA, are both antigenic in nature and much larger in size than the ligand. Thus, many or most of the antibodies produced in response to immunization with such a compound are directed against the carrier segment.

The present invention constitutes a much smaller carrier segment which has low antigenicity. Since there are both fewer epitopes and less antigenic epitopes presented to the immune system with the current invention, there is a net effect of making the ligand immunodominant. This results in a more robust immune response to the ligand of interest.

Production of Peptides: The present invention also advantageously allows the rapid production of large quantities of short peptides of defined sequences to be expressed as an insoluble fusion protein. The hydrophobic carrier segment can be cleaved and removed, or left attached. In addition to the uses listed above, leaving the carrier segment attached enables the peptide to be immobilized on hydrophobic surfaces, which may have utility for a wide variety of applications. The peptides can be used in all ways other short peptides are used, such as the neutralization of antibodies, direct immunization as discussed above, conjugation to other carriers for immunization, epitope mapping, as therapeutic agents, substrates for the assays of enzymes, and other applications. As is well-known in the prior art, fusion proteins can be processed by a variety of reagents to yield the desired peptide sequence separated from the carrier segment. An advantage of this invention is that removal of the carrier segment is facilitated by the low solubility of the carrier segment when the desired peptide is cleaved off.

Other advantages of the present invention over conventional peptide synthesis include lower cost of production of small quantities of peptides of defined sequences. Further, no toxic reagents are required in the process of the present invention. There also is less of a chance of modification of amino acid side chains, which has been demonstrated to be a problem with conventionally synthesized peptides.

The present invention also offers significant improvements over the current technology for making antibodies to peptides or proteins. The present invention makes it easier for an antibody to be made from a peptide sequence of a protein without requiring knowledge of the entire sequence of the target protein, as well as making antibodies with high affinity, specificity, and avidity to both the peptide and the parent protein from which the peptide was derived. Therefore, the basic problems involved with immunization, immunoaffinity purification of antibodies from polyclonal sera, peptide production and epitope mapping or identification can all be accomplished in facile, inexpensive, safe ways using equipment and methods very familiar to biologists not accustomed to working with peptides or synthesizing peptides.

The product of the present invention is designed to 1) produce a safe vaccine against infectious diseases, and 2) synthesize defined proteins against which antibodies can be raised for experimental, industrial, pharmaceutical and diagnostic purposes.

The present invention also is useful in the production of diagnostic reagents for use in diagnostic assays. The fusion protein, comprising the combination of carrier sequence and ligand, can be dispersed or immobilized on a variety of solid supports such as test tubes, microliter plate wells, dipsticks and the like. Moreover, using this technology makes it possible to generate longer peptides than feasible under standard chemical synthetic methods.

These and other aspects of the present invention will become evident upon reference to the following detailed description of the invention, the examples, and the attached drawings and photographs.

BRIEF DESCRIPTION OF THE DRAWINGS

FIG. 1 is an amino acid sequence of the preferred carrier protein [SEQ. ID. 1] of the present invention.

FIG. 2 is the preferred amino acid sequence of the polylinker segment [SEQ. ID. 3] of the present invention.

FIG. 3 is the amino acid sequence of the combined carrier segment and polylinker segment [SEQ. ID. 2] of the present invention.

In FIG. 5A, a purified fusion protein containing the carrier segment was assayed by high pressure liquid chromatography (HPLC). The desired protein peak is indicated by an arrow. The peak due to acetic acid adsorption is indicated with an open circle.

FIG. 5B is specifically a mass spectrogram of fusion protein purified from pMK160. As noted on FIG. 5B, the mass of the M+1 peak is extremely close to that predicted from the cDNA sequence.

DETAILED DESCRIPTION OF THE INVENTION

Definitions

Figure 4:
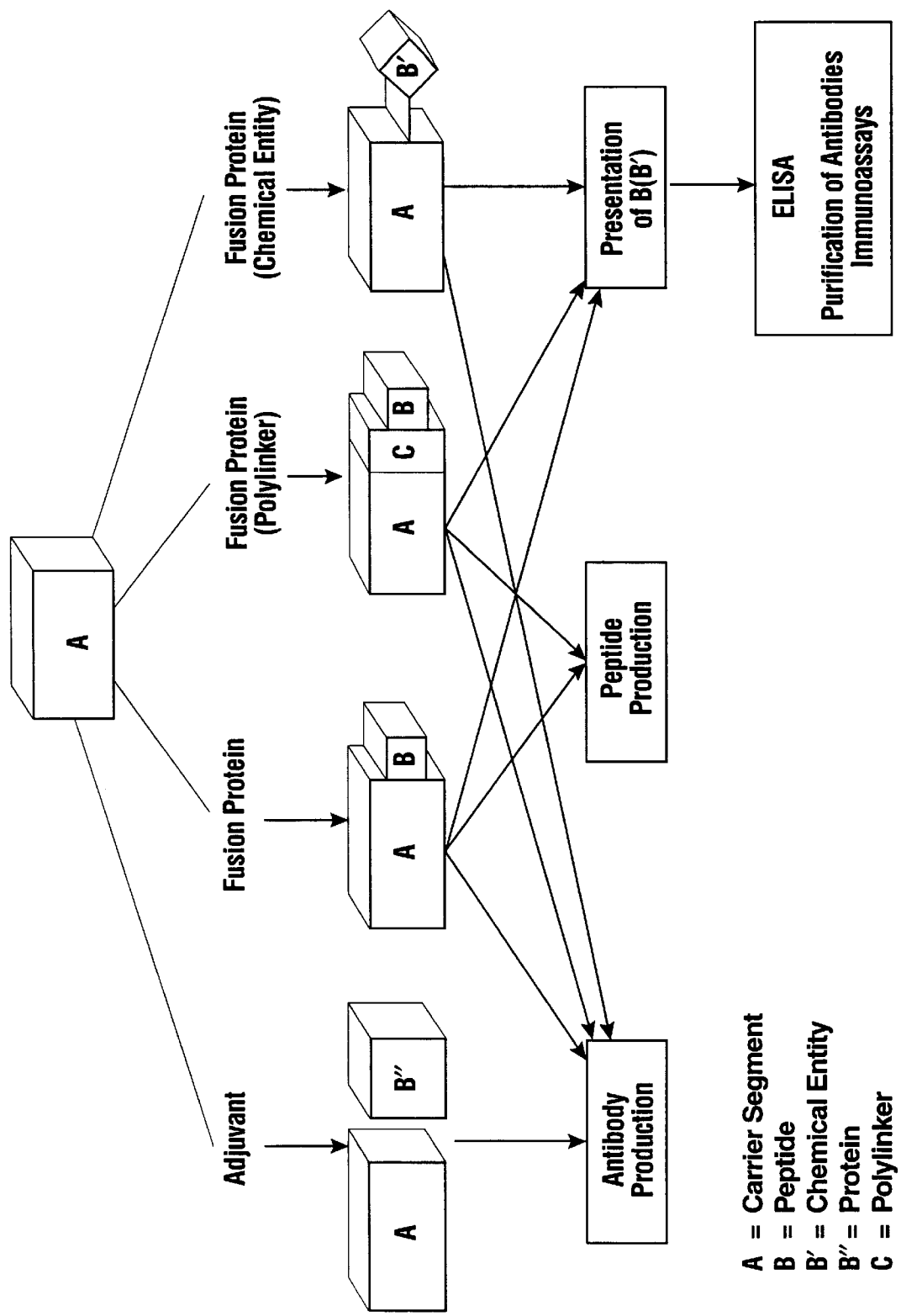
FIG. 4 is a flow chart illustrating the production and use of the fusion protein of the present invention.

The following definitions are provided to assist in providing a clear and consistent understanding of the scope and detail of the terms:

Adjuvant: A substance that nonspecifically augments the immune response to an antigen when mixed with the antigen prior to injection, or when injected separately but into the same site. Adjuvants are generally classified into five groups: oil adjuvants, mineral salts, synthetic polymers, liposomes, and natural substances.

Amino Acids: Amino acids are shown either by three letter or one letter abbreviations as follows:

| Abbreviated Designation | Amino Acid |
|---|---|
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

Antigen: A substance recognized by T- and B-cell receptors and which activates lymphocytes by interacting with the combining sites of T- or B-cell receptors.

Avidity: The overall tendency of antibodies to combine with antigens. Avidity is influenced by affinity, valency of antigens and antibodies, and the composition of antibodies.

Biological Activity: The capacity of acting or reacting in some specific way in a biological system.

Carrier Segment: A protein which allows coexpression of a heterologous peptide as a normal extension of or insertion in the polypeptide chain to form a fusion protein defined below, and/or which may be chemically coupled to a peptide, hapten, or other ligand to form a carrier protein conjugate defined below, and/or which may be coadministered with an antigen as described under "coadministration."

The carrier protein will generally have a molecular weight between about 10 to 50 kDa and preferably will not have an accessible internal cleavage site. The DNA and amino acid sequence of the preferred carrier protein is shown in FIG. 1 [SEQ. ID. 1].

Cloning Vehicle: A plasmid, phage DNA, cosmid or other DNA sequence which is able to replicate in a host cell, characterized by one, or a small number of, endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Coadministration: Mixing a desired antigen with a finely divided or soluble portion of the carrier segment, resulting in the physical entrapment of or association of the antigen with the carrier segment, followed by injection of the mixture into a host organism. Upon injection of the mixture, the antigen is considered to be coadministered. Alternatively, consecutive injections of the carrier and antigen into the same site may be considered coadministration.

Carrier Protein Complex: A preparation which consists of a carrier segment and a peptide, hapten, or other ligand, wherein the association between the two is noncovalent in nature. This includes physical entrapment of one by the other, electrostatic, hydrophobic, or affinity interactions, and chelates.

Carrier Protein Conjugate: A molecule which consists of a carrier segment and a peptide, hapten or other ligand, wherein the association between the two is any sort of covalent chemical bond. Such a molecule would typically be produced using a chemical crosslinking reagent. A subset of the carrier protein conjugate is a fusion protein as described below.

DNA Sequence: A linear array of nucleotides connected one to the other by phosphodiester bonds between the 3' and 5' carbons of adjacent pentoses.

Epitope: A small region of the ligand's surface that binds with the antibody. Epitopes also serve as antigenic determinants.

Expression: The process by which a polypeptide is produced by a gene or DNA sequence. It is a combination of transcription and translation. As it relates to proteins, expression refers to the directed synthesis of large amounts of desired proteins. Overexpression refers to production of a desired protein in amounts exceeding that normally produced by the cell in question.

Fusion Protein: A class of carrier protein conjugates which consists of a carrier segment and a chosen peptide, in which the connection between the two is a normal extension of or insertion in the polypeptide chain. A fusion protein could be produced by expression of a gene encoding the fusion sequence or by chemical coupling of the two in such a manner that a normal peptide linkage is formed.

Hapten: A substance of low molecular mass (typically lower than 4000 daltons) that can bind antibodies and induce immune response if covalently attached to a large carrier molecule.

Heterologous Peptide: A peptide which is not endogenous to the host selected, although this definition also includes endogenous peptides in cases in which overexpression of such is desired. Heterologous peptides are short relative to most proteins, generally having a molecular weight of less than about 10 kDa, and may be glycosylated, sialylated, phosphorylated, or the like. The peptide also will exhibit some form of useful activity, typically either biological activity, e.g., as a peptide hormone, or antigenic activity for use in recombinant vaccines and/or immunological assays. The peptide may either omit any cleavage site or may express a site in an inaccessible portion of the peptide, e.g., at a position of the peptide which is masked by another portion of the peptide, or by glycosylation, phosphorylation, or the like.

Immunogen: A substance capable of eliciting immune response.

Immunological Binding Activity: The specific capacity to bind to an antibody.

Inclusion Body: An inclusion body protein is one overexpressed in the host which at some stage of expression or purification is visible by phase contrast microscopy as a precipitate, regardless of the physical state of the protein at the time it is referenced. A further description of inclusion body can be found in U.S. Pat. No. 4,512,922 to Jones et al., which is incorporated herein by reference for a description of inclusion bodies, and which refers to inclusion bodies as "refractile bodies."

Isotypes: Classes or subclasses of antibody defined by shared epitopes present on all molecules of the heavy chains in that antibody class or subclass in a given animal species, e. g., IgM, $IgG_2$, and $IgG_3$.

Ligand: A molecule that binds a specific receptor or enzyme. Examples include proteins, peptides, haptens, polysaccharides or other biomolecular entities, and are known to interact with antibodies.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine (A), guanine (G), cytosine (C), and thymine (T). The four RNA bases are A, G, C, and uracil (U).

Nucleotide Base Sequence: A linear array of nucleotides in a DNA molecule commonly prepared from four DNTP precursors: dATP, dCTP, dGTP and dTTP. Modified bases, other than the usual four found in DNA, also may be incorporated.

Peptide: A compound consisting of 2–50 naturally occurring or synthetic amino acids which also can be further modified, as described above, which is covalently linked through peptide bonds formed from the α-carboxyl group of one amino acid and the α-amino group of the next amino acid by elimination of a molecule of water. The amino acids can be either naturally occurring amino acids as described above, chemically synthesized variants of such amino acids such as norleucine, or modified forms of these amino acids which can be altered from their basic chemical structure by addition of other chemical groups which can be found to be covalently attached to them in naturally occurring compounds. Some of the modifications so attached include: phosphate groups, lipid groups, nucleotide groups, and polymers of sugars and will include other modifications known to those skilled in the art.

Plasmid: A nonchromosomal, double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (TETR) transforms a cell previously sensitive to tetracycline into one which is resistant to it. A cell transformed by a plasmid is called a "transformant."

Recombinant DNA Molecule or Hybrid DNA: A molecule consisting of segments of DNA from different sources which have been joined end-to-end outside of living cells and are able to be maintained in living cells.

BASIC INVENTION

The basic invention is directed to the construction of a carrier protein conjugate or a carrier protein complex. The carrier protein conjugate or complex comprises a first amino acid sequence, wherein the first amino acid sequence is substantially non-naturally occurring and insoluble, and a ligand having biological activity or immunological binding activity.

CARRIER SEGMENT

Properties of Carrier Segment

The present invention is specifically directed to a proteinaceous carrier segment which will be referred to as a "carrier segment" or "the segment." The carrier segment described in this invention has free amino and carboxy termini, although that is not necessary for most of the purposes described. The carrier segment has been designed to have several properties that are of importance to the present invention. The carrier segment is hydrophobic. Since the carrier segment dominates the solubility behavior when attached to short peptides and ligands, conjugates containing it are sparingly soluble in neutral aqueous solutions.

The carrier segment and fusion proteins containing it are expressed to high levels in *E. coli* and are made as insoluble protein granules known as inclusion bodies. The protein found in these inclusion bodies is easy to purify in large quantities using techniques known to the art. The carrier segment itself has low antigenicity when injected into animals, but will adequately display an attached ligand to the immune system of an animal. The carrier segment also lacks many sites of cleavage recognized by proteases with specificity for a single amino acid, and is soluble in some solutions that allow cleavage by chemicals and enzymes, e.g., urea, SDS, formic acid, and formamide.

Design of Carrier Segment

A carrier segment with the above favorable properties was designed in several defined steps. By using these steps and one extra step not needed in this case, a researcher could design other carrier segments starting with different proteins. A highly expressed protein sequence was identified for which an expression vector was available (in this case gene 10 protein of phage T7, encoded by vector pGEMEX-1).

The initial protein in this case was expressed at about 100 mg/l of culture in *E. coli* cells. Next, the designed protein sequence was truncated to 79 amino acids, not counting the polylinker amino acids as described later. Making the sequence smaller, it is less likely to contain antigenic sites to start with. There appears to be a length minimum at around 65 amino acids below which good expression is not obtained in *E. coli.*

The truncated sequence was further modified by substituting uncharged amino acids or histidine for the charged amino acids lysine, arginine, aspartic acid, and glutamic acid. Any tryptophan or cysteine residues were changed to any uncharged amino acid, and all methionines, except for the amino terminal one (necessary if expression were to be accomplished in *E.coli*), were substituted with any uncharged amino acid, most often valine. In general, a replacement amino acid was selected which did not require great changes in the DNA sequence of the expression vector; usually only the third base of the codon was changed. Other slight changes (1 amino acid insertions) in amino acid sequence were made to accommodate cloning of the DNA encoding the carrier segment into the expression vector, described later.

Thus, the salient design feature of the carrier segment is that it is truncated to about 79 amino acids, not counting the polylinker amino acids as described later, and lacks at least two and preferably all of the following list of amino acids: glutamic acid, aspartic acid, lysine, arginine, methionine (except for the single methionine placed on the amino terminus of the segment which is required for translation initiation in E.coli), tryptophan, and cysteine. The lack of these amino acids is accomplished by substituting uncharged amino acids. If the starting protein were very hydrophilic and especially if it contained many uncharged hydrophilic amino acids such as threonine and serine, following the above design rules might not result in a protein that was hydrophobic enough to have the desired low solubility. In this case, a further design rule would be to systematicaiiy stitute hydrophilic amino acids with more hydrophobic ones such as leucine, isoleucine, valine, and alanine, until the desired low solubility was achieved.

Not all of the charged amino acids must be eliminated. In some cases, it is desirable or necessary to leave one or more charged amino acids in the carrier segment. For example, in order to clone a peptide-encoding DNA sequence into the expression vector for the carrier segment, the vector must contain some sites where restriction enzymes can cut. Usually several such sites are clustered in a single locus in the vector, creating what is commonly called a polylinker. There are often a few charged amino acids encoded by the DNA sequence in such polylinker sequences. Thus, the ideal carrier segment is devoid of charged amino acids except at the polylinker site.

As stated above, it is desired to create a carrier segment having only enough size to accomplish the desired purpose. Suitable carrier segments have been produced which have a length between about 65 and 100 amino acids long.

The preferred amino acid sequence of the carrier segment consists of 79 amino acids [SEQ. ID. #1] and is illustrated in FIG. 1. The amino acid sequence of the carrier segment also can include a polylinker segment (FIG. 2 [SEQ. ID. 3]) and thus be a combination of the carrier segment of FIG. 1 and the polylinker segment of FIG. 2, as illustrated in FIG. 3 [SEQ. ID. 2.].

Direct Use of Carrier Segment Described Above

As described later, a researcher will wish to modify the DNA vector encoding the carrier segment to include polylinker segments or fused peptide sequence of interest. The carrier segment also can be produced without further amino acids being added or modified and advantageously used in several ways as described below.

As Part of a Carrier Protein Conjugate: The carrier segment can be fused to a second chemical entity or ligand. As described later, this conjugate can be made by chemically coupling a ligand to the purified carrier segment. The conjugates thus prepared may be used for immunizations, coating of surfaces, receptor binding, and many of the other ways described elsewhere in this invention.

As an Adjuvant: The carrier segment also has use as an adjuvant, i. e., without necessarily being fused to a ligand. The carrier segment can be coadministered with a protein for injection into a host animal. Typically, the carrier segment will work best with high molecular weight proteins or other polymers and biopolymers. Preferably, the molecular weight of the coadministered molecule is at least about 4,000 daltons.

The carrier segment is mixed with the desired molecule and coinjected into animals. This is advantageous in that the carrier segment nonspecifically augments the specific immune response to the desired molecule, resulting in the generation of a stronger immune response of the animal to the desired molecule. This property, along with others, indicates that the carrier segment demonstrates activities which define it as an adjuvant.

LIGAND

The ligand can be a second peptide segment, a nonpeptide chemical moiety or hapten, or a mixed composition consisting of both a peptide segment chemically linked to a nonpeptide chemical entity.

Examples of chemical moieties which are available for fusion to the carrier segment include fluorescent moieties such as rhodamine, fluorescein, dansyl, and derivatives of such compounds; mono and polysaccharides; pharmaceutical agents; and derivatives and metabolites of such agents; environmentally hazardous chemicals and derivatives and metabolites of such agents, pesticide chemicals and derivatives and metabolites of such agents, and lipids.

The chemical moieties are chemically attached to the carrier segment by a variety of means discussed in more detail later. Such means would include use of pre-derivatized compounds designed to couple the desired moieties to biomolecules, use of chemical crosslinking agents, or expression as a fusion protein if the ligand is a peptide segment. A wide range of reagents for coupling ligands to biomolecules are commercially available from corporations such as Molecular Probes (Eugene, Oreg.) and Pierce Chemical (Rockford, Ill.). Some of these reagents also allow for the coupling of multiple copies of the ligand to the carrier segment.

The ligand may have either immunological binding activity (otherwise known as "immunologically active") or other biological activity The ligand may have a single activity, for example antigenicity, receptor binding activity, therapeutic activity, or targeting activity, i.e., the ability to move to a given locus in a host animal after administration. The ligand also may have a combination of two or more such activities.

If the ligand is a peptide, it may be an amino acid sequence known to the art or yet to be developed or identified. Examples of the amino acid sequence include derivations from a lymphokine gene such as an interferon gene or a gene coding for an antigen of an infectious agent such as a virus, bacterium or other parasite. For example, it may be an antigen of influenza virus, an HIV virus, a rabies virus, etc. It also may be a fragment of the above antigens or a peptide resulting from a chemically synthesized coding sequence such that the resulting peptide has substantially the same antigenicity as the above antigens or fragments thereof. Reference is made to U.S. Pat. No. 5,008,373 to Kingsman et al., which is incorporated herein by reference for a disclosure of examples of suitable amino acid sequences.

EXPRESSION VECTOR

Referring to FIG. 4, the production of various proteins of interest is achieved by expressing in host cells a proteinaceous carrier segment A or carrier segment-containing fusion protein A+B, which is then collected and purified, and then either used directly, linked to a ligand B, coadministered with a ligand B", or cleaved to remove the carrier segment B'.

The process involves the engineering of a recombinant DNA vector which, upon transformation into a suitable host, and subsequent expression, produces the carrier segment or carrier segment-containing fusion protein in abundance. Although the preferred host cells are procaryotic cells such as E. coli, the invention also includes production of carrier segments or carrier segment-containing fusion proteins in a variety of host cells; for example, yeast cells such as S. cerevisiae, animal cells such as Chinese hamster ovary (CHO) cells, or COS cells containing a suitable expression vector that directs production of the desired protein.

Construction of suitable vectors and cassettes containing the desired coding and control regions employs DNA manipulations (oligonucleotide synthesis, ligation, restriction) which are well understood in the art. Isolated plasmids, DNA sequences, or synthesized oligonucleotides are cleaved, tailored, and relegated in the form desired.

A protein-coding cassette is constructed which encodes the desired carrier segment. The protein encoded by the cassette is about 10 kilodalton (10 kD) in molecular weight, and holds to the design principles of the carrier segment described above; namely, in brief that it has low solubility and antigenicity due to the selective removal of many charged amino acids. The preferred carrier segment protein and DNA sequence is illustrated in FIG. 1 [SEQ. ID. 1].

The protein-coding cassette for the above-designed carrier segment is then subcloned into a suitable expression vector. Usually this is a plasmid vector, although other systems could be used depending on the host organism used for expression. In the examples presented, the expression vector is a modification of a vector known as pGEMEX-1, which is described in Promega Corporation's (Madison, Wis.) catalog. The plasmid vector is a derivative of the well-known pBR322 vector derived from an E. coli species by Bolivar et al (1977). Expression of the carrier segment protein is driven by a promoter for T7 RNA polymerase. Other plasmids which contain replication sites, control sequences, and antibiotic resistant markers derived from a species compatible with the host also could be used. Commonly used prokaryotic control sequences which are defined herein include promoters for transcription initiation and termination along with ribosome binding site sequences, and include such promoters as the beta-lactamase promoter.

The expression systems useful in eukaryotic systems of the invention comprise promoters derived from appropriate eukaryotic genes. A class of promoters useful in yeast, for example, include promoters for synthesis of glycolytic enzymes, including those for 3-phosphoglycerate kinase.

Even more advantageous to the present invention is the use of an expression vector construct which contains the DNA encoding the carrier segment and which has this segment followed by a nucleotide segment, called a polylinker segment (C in FIG. 4), which contains the recognition sequence of at least one restriction endonuclease enzyme and which does not contain translation termination codons within the known reading frame of the carrier segment and the DNA encoding the restriction endonuclease site. Such a polylinker segment is advantageous in that the DNA encoding the expression vector can then be cut at specific sites in the polylinker using the restriction endonuclease, and a DNA segment encoding a desired peptide ligand can be inserted into the expression vector at this point. In such a situation, one must ensure that the resulting vector will encode for a fusion protein containing the carrier segment and peptide of interest, that there will be no translation termination codons in the reading frame in the intervening DNA between the DNAs encoding the carrier segment and the ligand, and that the inserted DNA should include a translation termination codon at the end of the desired fusion protein. The knowledge concerning the proper design and use of polylinkers in the production of fusion proteins is well-known in the art. If desired, confirmation of the amino acid sequence of the resulting construct can be done by determining the DNA sequence of the resulting vector by use of methods well-known in the art.

The preferred DNA sequence of the polylinker and the amino acids encoded by the polylinker sequence is illustrated in FIG. 2 [SEQ. ID. 3]. As discussed earlier, some of the codons in the polylinker segment encode charged amino acids. This is not detrimental to the performance of the fusion protein.

The preferred DNA sequence of the complete vector plus the polylinker consists of the sequence shown in FIG. 3 [SEQ. ID. 2], wherein the remainder of the vector comprises pGEMEX-1, in which the DNA sequence from 5 to 905 are replaced with the sequence described in FIG. 3 in such a manner that the ATG codon (Met) is proximal to the T7 promoter sequence in the pGEMEX-1 vector. Note that when peptide-encoding oligonucleotides are cloned into the polylinker with a translation terminator at the end of the desired peptide, some of the amino acids on the carboxy terminal end of the sequence of FIG. 3 will not be present in the fusion protein. When fusion peptides are produced by cloning into the Notl/Hind3 site described in Example 2, the C-terminal 8 amino acids are missing. This does not adversely affect the properties of the fusion proteins.

EXPRESSION STRAIN

The proteins of the invention may be expressed in either prokaryotic or eukaryotic systems. Prokaryotes are most frequently represented by various strains of E. coli. The preferred host strain is BL21(DE3) plyss, a strain commercially available from Novagen Corporation (Madison, Wis.). However, other microbial strains also may be used, such as bacilli (for example, B. subtilis), various strains of Pseudomonas, and others. Common eukaryotic expression strains would include strains of yeast, and baculovirus expression in insect cells. One possible advantage of the invention is that the deposition of the expressed protein in insoluble deposits may allow expression of fusion proteins that might otherwise be more detrimental or toxic to the cell.

Transformation

Depending on the host cell used, transformation is accomplished using standard techniques appropriate to such cells. The calcium chloride treatment, such as described by Cohen (1972) or the RbCl method described in Maniatis et al. (1989) is used with prokaryotes which contain substantial cell wall barriers. The preferred host strain is BL21(DE3) plysS, and the transformation protocol used is the one recommended by the manufacturer (Novagen Corp., Madison, Wis.).

Verification of Construction

After transformation, successful transformants are selected by ampicillin (preferred), tetracycline, or other antibiotic resistance or using other markers depending on the plasmid construction as is understood in the art. Plasmids from the transformants are then prepared according to the method of Clewell et al. (1969). The sequence of the plasmid can then be verified by standard DNA sequencing methods well-known to the art.

PRODUCTION AND PURIFICATION OF CARRIER SEGMENT AND FUSION PROTEINS

Expression/Cell Harvest

Transformed expression strains are grown in shake flasks or fermentors to a suitable density. Then, expression of the desired protein is stimulated using the appropriate induction protocol. In the preferred case, the induction is accomplished by the addition of isopropyl-B-thiogalactopyranoside (IPTG), a standard inducer for T7 expression strains. In some cases, addition of agents such as rifampicin, which block the action of the host RNA polymerase, may cause an increase in production of the desired protein. Alternatively, an expression system may be used in which the expression is unregulated. The time for harvest of cells can either be predetermined, or checked by monitoring protein expression in real time.

Expressing cells can be harvested by centrifugation and stored up to several weeks at −70° C. before breaking them and purifying the protein contained therein.

Purification of Carrier Segment and/or Fusion Proteins

Since the expressed protein is in general much less soluble than the other proteins in the cell, it is relatively easy to purify from prokaryotic cells using standard techniques known in the art. First, the cells are lysed by enzymatic or mechanical means in a buffer. The preferred method is sonication, although any other lysis method will work, as long as lysis is complete and DNA and RNA are sufficiently fragmented so as not to pellet upon centrifugation. Preferred buffers contain Tris buffer at pH 7–8, isotonic saline, and dithiothreitol (DTT) to maintain all cell proteins in a reduced state. After sonication, detergent is added to the mixture to solubilize most lipids and proteins, and the mixture is centrifuged; it is preferred to use a centrifuge speed of greater than 10,000G for 10 minutes. The desired protein is then found in the pellet fraction at a high degree of purity.

Higher purity is usually obtained by washing the pellet in a second wash solution, often containing a different agent or detergent. Washing is accomplished by resuspending the pellet in the fresh buffer followed by centrifugation as above. The preferred first detergent is sodium deoxycholate (NaDOC), and the second preferred detergent is Triton X-100.

After the detergent washes, the pellet can be washed either with the above buffer or with phosphate-buffered saline (PBS) to remove trace detergent, then resuspended in a volume of a desired buffer for storage or use in any of the ways described elsewhere, including immunization. The advantage of the low solubility of the protein is that the purification is easy and quick, and requires very little specialized equipment.

The proteins purified by the above method are ready for use in any or all of the applications contemplated in the invention, including but not limited to the following; immunization of animals, use as an adjuvant, coupling to other ligands, use as a protease inhibitor, immobilization on hydrophobic surfaces, use as an enzyme substrate, and use in peptide production after cleavage.

PRODUCTION OF CARRIER PROTEIN CONJUGATES FROM PURIFIED CARRIER SEGMENTS AND DESIRED LIGANDS

The purified carrier segment either can be used directly for the applications described under "carrier segment", or it can be derivatized with a variety of ligands described under "ligand" using the strategies described below. These include the use of prederivatized ligands, chemical coupling reagents, and crosslinking reagents.

Use of Prederivatized Ligands

In many cases, the linkage of the desired ligands to the carrier segment can be accomplished by use of commercial derivatives of such compounds which have been produced to facilitate the addition of such compounds to molecules, such as fluorescein isothiocyanate, NHS-Rhodamine (Pierce Chemical Co., Rockford, Ill., Products 46110 and 46102, respectively.), and Sulforhodamine 101 acid chloride (Aldrich Chemical Co., Milwaukee, Wis., Product 28,406-8) Many of these compounds have been specifically synthesized so that they react with the chemical groups which are found in proteins, such as the amino-terminus, carboxy-terminus, the hydroxyl functions of the amino acids serine and threonine, in such a way as to covalently attach the desired chemical moiety to the protein. The catalogs of many corporations such as Molecular Probes (Eugene, Oreg.) or Pierce Chemical Co. (Rockford, Ill.) have a plethora of such compounds with known reactivities that can be used in many ways to selectively add such compounds to the carrier protein.

One advantage of the carrier segment in this regard is that since many reactive amino acid side chains are not present, one can obtain a more selective localization of the site of ligand addition.

Use of Chemical Coupling Reagents

Another method for the formation of a carrier protein conjugate is to incubate the carrier segment and the ligand in solution with chemical entities which can facilitate the chemical coupling of the two segments without being included in the final product. One such method would be through the use of reagents which couple a free carboxylic acid moiety to an amino group. The carrier segment described in this invention has a free amino terminus and carboxy terminus, and thus can be linked to a ligand or peptide through the use of such reagents if the ligand contains either a free carboxylic acid group or amino group somewhere in its chemical structure. One such reagent which is commonly used to form such linkages is 1,3 dicyclohexylcarbodiimide (DCC) (Aldrich Chemical Co., Milwaukee, Wis., Product D8,000-2). When DCC is used in such a coupling reaction, an amide bond between the carrier segment and ligand is formed comprising the original carboxyl group and the amino group, with a concomitant expulsion of a water molecule. Thus, the final conjugate does not retain any part of the DCC reagent that was used to create the conjugate. Several different reagents having similar properties have been extensively described in the literature.

Use of Crosslinking Reagents

Another method for the formation of a carrier protein conjugate is to incubate the carrier segment and the ligand in solution with chemical entities which can facilitate the chemical coupling of the two segments and are included in the final product to various degrees. The scientific interest in the use of such compounds has resulted in the development of many different reagents which provide different reactivities and advantages to the user and allow the user to select the particular reagent which will be most advantageous for their particular application. Reference is herein made to Tae, H. J., et al., (1983) for a description of the composition and use of many such reagents.

Such reagents are also widely commercially available through such suppliers as Aldrich Chemical Co., Milwaukee, Wis. and Pierce Chemical Co., Rockford, Ill. Examples of such reagents include dimethylsuberimidate (DMS) and m-maleimidobenzoyl-N-hydroxysuccinimide ester (MBS) (Pierce Chemical Co., Rockford, Ill., Products 20668 and 22310, respectively).

If multiple copies of some chemical entity attached to the carrier segment are desired, but not by attaching the chemical moiety to chemical groups which are present in multiple copies within the sequence of the carrier segment, the user can form such a multiple derivatized carrier segment in several way. One way this can be done would be through the attachment of a peptide segment to the carrier segment which has multiple chemical groups which could be used for the formation of chemical crosslinks of the types described above. For example, a peptide sequence having three or more lysine residues in a short peptide sequence could be attached to the carrier segment. The new fusion made above could then be crosslinked to the chemical moiety of interest using these three new primary amino groups in the structure of the new fusion material and chemical entities which crosslink materials to amino groups.

Uses of Conjugates Other than Immunization

In addition to producing a material which could be used to generate antibodies to these chemical moieties, there are other advantages to coupling such materials to the carrier protein. Many of these materials are difficult to bind to particular materials, such as the plastics which are used to manufacture microtiter plate wells. The inability to bind such ligands to these materials in a way that allows them to be specifically bound by antibodies complicates their measurement using techniques such as ELISA testing. However, the carrier protein conjugates containing such ligands can be readily bound to such materials in such a way that the recognition of the chemical moiety by an antibody or enzyme is not inhibited. Thus, the ease of formation of such conjugates and the ability of such conjugates to present the ligands to antibodies and enzymes allow applications for the chemically coupled carrier protein conjugates beyond their use as immunogens.

USE OF CARRIER SEGMENT-CONTAINING FUSION PROTEINS FOR THE PRODUCTION OF PEPTIDES

The present invention also is directed to the production and purification of biologically or immunologically active peptides using the fusion protein produced by the combination of the carrier segment and the desired peptide. This part of the invention basically relies on the combination of the carrier segment and the peptide with an intervening, cleavable amino acid sequence, which allows for the liberation of the peptide from the carrier segment using reagents which can sequence-specifically cleave protein sequences at peptide bonds. The desired peptide can then be easily separated, for example, by filtration or centrifugation, from the carrier segment, which is largely insoluble in aqueous solutions. Thus, there is provided a method producing a substantially pure and active peptide as described in the present invention. Unless otherwise described, the term "active" used alone is intended to mean either (or both) biologically active or immunologically active.

The carrier segment of the present invention provides the user with two important advantages: 1) it does not contain several of the common amino acids that can be attacked by sequence-specific reagents to cleave protein segments; and 2) the low solubility of the carrier segment allows the separation of the carrier segment from the released peptide to be easily accomplished in many instances. For example, if such a fusion is made which has the peptide fused to the end of the carrier segment, and the desired peptide does not contain any lysine residues, then a fusion protein can be expressed with a single lysine at the junction of the carrier segment and the desired peptide. The resulting fusion protein can be purified as described above, and then digested using proteases well-known in the art, such as trypsin or endoprotease Lys C to cleave the fusion protein at the carboxy side of the lysine. This cleavage reaction would yield two product peptides; one would consist of the insoluble carrier segment with a lysine at its carboxy terminus, and the other would consist of the desired peptide, which in most cases will have considerable greater solubility in aqueous solutions.

Vector Construction

The fusion protein is created by methods discussed in the previous section, with the added design principle that the user designs the oligonucleotide encoding the new portion of the fusion protein so that an amino acid is present at the junction between the fusion protein and the peptide of interest that is lacking in both the carrier segment and the desired peptide. The amino acids designed to be absent from the carrier segment described earlier are methionine (except for the amino terminal met), lysine, arginine, tryptophan, glutamic acid, aspartic acid, and cysteine. Since reagents are available for cleavage of protein sequences at each of the amino acids missing in the carrier segment, this allows the user the luxury of choosing which of several amino acids they wish to place at the cleavage site in many cases. It is very desirable to use one of the amino acids that is not present in either the peptide or the carrier segment, so that only two products of the reaction are possible.

Expression/Purification

This would be accomplished using means described above.

Digestion of Fusion Protein

The insoluble fusion protein must first be solubilized in reagents which are compatible with the cleavage reagent desired. Such reagents include aqueous solutions containing chaotropes (4 M urea, 4 M guanidine hydrochloride), detergent solutions (1% SDS, 1% sarkosyl), or mixed organic acid/water solutions (50% acetic acid, 70% formic acid). Next, the solutions are treated with various chemical or enzymatic agents capable of cleaving the peptide bond at the desired amino acid (using reagents such as endoproteases Arg-C, Glu-C, Lys-C, Asp-N), or chemical reagents such as CNBr (cuts at Met), BNPS-skatole (cuts at Trp), or dilute acid (cuts at Asp-Pro)). For all of these agents, solutions are available which will dissolve the fusion-protein and which will allow the reagents to act upon the fusion protein.

Alternatively, a suspension of the fusion protein also could be treated with the reagent. Even though the fusion protein is only sparingly soluble, some of the fusion protein is in solution and/or accessible to the reagent. Longer incubation of the reaction mixture will eventually result in complete cleavage of all of the fusion protein. Reaction time courses can be monitored either by SDS gel (observing the change in molecular weight of the fusion protein), or by reversed-phase HPLC.

Separation of Peptide from Carrier Segment

To remove the bulk of the carrier segment from the peptide, all that is required is to remove the solubilizing agent and to separate the insoluble carrier segment. Removal of the solubilizing agent can be done by dialysis, diafiltration, dilution, lyophilization, or other means readily available to the user. Removal of precipitated carrier segment may be made by filtration, centrifugation, or settling. The supernatant solution will contain substantially pure peptide, which in many cases can be used as is, or which can be further purified by methods standard to the art of peptide purification. If removal of trace remaining carrier segment is desired, passage of the supernatant over a hydrophobic resin such as phenyl-Sepharose (Pharmacia Corp., Uppsala, Sweden) will selectively remove the carrier segment, leaving the peptide in the flow-through fraction.

A substantial advantage of this approach is that the user does not need access to peptide synthesizers, and there also is a lower chance that the purified peptide contains deleterious side chain modifications. A recent test of biotechnology core facilities indicated that deleterious side chain modifications of synthetic peptides are extremely common; 50–60% of the peptides tested contained a modified peptide as the major component, even when the peptides were purified after synthesis (Smith, A. J. et al., 1992). The major cause of this was determined to be incomplete deprotection of amino acids after synthesis. The method of invention never adds these groups so this problem is avoided completely.

USES OF CARRIER PROTEIN CONJUGATES AS PEPTIDE EQUIVALENTS

Production of Specific Protease Inhibitors

As previously discussed, there are a number of applications wherein the carrier segment is best either left attached to the desired peptide or removed from it. There are a few applications in which either embodiment is allowable. One of these is the production of specific protease inhibitors. If a desired protein whose sequence is known is observed to be proteolytically cleaved at specific sites, the usual way to block cleavage is to add protease inhibitors. Since no single inhibitor can fully block the action of all proteases, screening of multiple inhibitors is required. In addition, such agents are often expensive to use at larger scale as well.

If the approximate location of the cleavage site is known, one then can create large quantities of fusion protein using methods described earlier which contains a peptide spanning the approximate site of protease cleavage. Addition of this fusion protein, or peptide prepared from the fusion protein, will protect the protein of interest from cleavage by mass action, i.e. the addition of a vast excess of protease sites. The resultant fragment containing the carrier segment will then be easily removable by any of the methods noted previously.

Use in Studies of Protein Modification Enzymes and Protein-Protein Interactions

Another use of the carrier protein conjugates is as substrates for enzymes that covalently modify amino acid side chains of proteins, such as kinases, phosphatases, glycosidases, and the like. With the carrier segment removed, these peptides can be used in all of the standard assays typically used in the study of such enzymes. With the carrier segment attached, the peptides will be substantially insoluble and capable of being immobilized to solid supports, which may have advantages in developing assays in microtiter plates. Similarly, peptides increasingly are being used in studies of protein-protein interactions, in which case the selected peptide is usually a region of a protein which interacts with the selected region of a second protein. Again, either the free or carrier segment-attached peptide may be used for such studies. One additional potential advantage of the system described for these studies is that variants on the known peptide sequence may be readily prepared and tested, either by preparing alternative cloned sequences through methods known to the art, or by using amber suppression expression systems which can substitute several different defined amino acids at a single site using a single vector as a starting point (Interchange kit, Promega Corp, Madison, Wis.).

Use in Protein Purification by Affinity Interactions

A large number of proteins interact with each other through specific protein-protein interaction domains. A carrier protein conjugate in which the ligand contains one of these domains could be immobilized and used in an affinity mode to selectively bind a protein of interest. This method also can be used in the case where the peptide used has been identified by screening of a peptide display library using techniques well known to the art. The advantage in this usage is that large quantities of the desired peptide sequence can be easily and inexpensively produced, purified, and immobilized.

Use in Cell Sorting

Finally, some cells display receptors on their surfaces which are indicative of their status with respect to proliferation, differentiation, or other characteristic. If a peptidic ligand is known for these receptors, carrier protein conjugates might be used to separate the indicated cells from a mixed population. This could be by passage of cells over a surface coated with the carrier protein conjugate, settling of cells comixed with a fine suspension of the conjugate, or by mixing cells with a dilute solution of the conjugate followed by passage over a hydrophobic resin. Here, the ligand is adapted to selectively bind to a specific cell type or cells in a specific state of growth.

USES OF CARRIER PROTEIN CONJUGATES AS I UNOLOGIC REAGENTS

Production of Antibodies

The present invention also is useful in that it is adapted to be used as an immunogen for the generation of antibodies. The antibodies may be polyclonal or monoclonal. The monoclonal antibodies are produced by hybridoma cells, and polyclonal antibodies are produced in host animals according to methods known to the art. Because of the low antigenic nature of the carrier sequence, it is more likely that the antibodies will be raised against the ligands of interest rather than the carrier segment. In the case of monoclonal antibodies, this should allow a higher success rate and therefore less costly screening. In addition, the immunization with the carrier protein conjugate may be advantageous over injection of native proteins in that the epitope of the resultant monoclonal antibody is predefined. Thus, an experiment would prepare several carrier protein conjugates containing different ligand segments of the desired protein, inject into host animals, and proceed to make monoclonal antibodies using the animal with the best initial polyclonal antibody titer. Moreover, using this technology the dose of immunogen influences antibody isotype which allows for enrichment of the desired antibody isotype.

The present invention is further directed to the production of antibodies raised against particles of the invention which are antigenic. The antibodies may be polyclonal (obtained for example by injecting antigens into a rabbit) or monoclonal, produced by hybridoma cells in accordance with the invention. The particulate antigens are polyvalent in nature. Therefore, it is more likely that in vitro immunization can be achieved more readily than with other forms of antigen. This may facilitate the production of human monoclonal antibodies.

Hybridoma cells then may be prepared by fusing lymphoid organ cells from an immunized animal with a tumor cell. Appropriately secreting hybridoma cells may thereafter be selected (Kohler & Milstein, 1976).

The present invention also is directed to the production of antibodies by taking the specific carrier segment, fusing any ligand and injecting the resultant carrier protein conjugate into a host animal which will produce antibodies to the ligand. The novelty of this invention is that an antibody to any ligand can be made if the ligand is fused to the specific carrier segment of the present invention.

The desired carrier protein conjugates are created by the combination of the carrier segment and the ligand. A fusion protein for antibody production does not need a cleavage segment between the carrier segment and the peptide. In antibody production, antigens typically are injected into the host animal intact, so there is no need to separate the peptide from the carrier segment. In fact, the carrier segment is required to elicit T-cell help. Sub-milligram amounts of the fusion protein are then injected into the recipient animal.

Administering (Injecting) Carrier Protein Conjugates and Complexes as Antigens

The immunogens prepared as described above can be administered parenterally. Parenteral administration can be carried out intradermally (ID), i.e., by injecting the substance into the skin; subcutaneously (SC), i.e., beneath the skin; intramuscularly, (IM), i.e., into the muscle; intravenously (IV), i.e., into the vein; or intraperitoneally (IP), i.e., into the peritoneal cavity. Peroral administration, i.e., through the mouth, can be used in some circumstances when the digestive enzymes in the stomach do not destroy the immunogen before it can activate the immune system.

Usually, immunogens are suspended in adjuvants to enhance the nonspecific immune response and entrap the antigen at the site of injection. However, the present invention has sufficient intrinsic adjuvant activity to obviate the need for additional adjuvant. When immunogens are injected into the animal body, the majority of the carrier protein conjugates remains at the spot of injection. Gradually, however, antigens leach from the point of injection and are transported through the bloodstream to the regional lymph node. The antigens are released from the point of injection by leaching and by the actions of cells in the region. The immune cells interact because of the irritation in that region causing the immunogen to be transported to its destination in the lymphatic system.

As discussed above, submilligram amounts of immunogen are sufficient to elicit a useful immune response. This dosage level is comparable to that used for administration of immunogens prepared by other methods, however as little as 10 μg of carrier protein conjugate have been shown to elicit a robust humoral immune response in the absence of adjuvant. Although the lower dosage range may vary for different ligands, this represents a much lower amount of adjuvant free immunogen required than by many traditional methods known to the art.

Although the normal immunization schedules known to the art for different host animals are appropriate for the carrier protein conjugates of this invention, a single administration of 200 μg of immunogen also has been shown to be effective in eliciting a robust humoral immune response to the ligand. This can have significant advantages when dosage administration is technically difficult or time-consuming.

As previously discussed, the carrier segment acts as a carrier to elicit T-cell help for the ligand, and as an adjuvant for the attached ligand. The carrier segment also may exert these effects on a ligand which is admixed rather than covalently attached. In this case, a dilute suspension of carrier protein segment is vigorously mixed with the desired immunogen, and the complex is then injected into the host animal.

Vaccine

The immunogens prepared in accordance with the invention may be useful in the preparation of vaccines. In this case, the carrier protein conjugate may contain a portion of the amino acid sequence of an antigen of an infectious agent or a ligand from an environmental toxin for instance. The vaccine comprises a particulate immunogen described above and a physiologically acceptable excipient, such as sterile pyrogen-free physiological saline.

The ligand present in the carrier protein conjugate can be adapted to be administered to any vertebrate immune system, e.g., rabbit, mouse, goat, rat, hamster, dog, cat, cattle, sheep, chicken, pigs and humans. It is within the scope of the present invention to combine virtually any ligand with the carrier segment. The optimal regimen for vaccination may differ from those discussed above for antibody production.

Uses of Carrier Protein Conjugate to Purify Antibodies

Two different methods can be used to purify antibodies using the fusion protein. Inclusion bodies comprised of the fusion protein can be mixed with crude antibody preparations to the target ligand. The solution can then be spun to pellet the added inclusion bodies and washed. This process removes all of the antibodies and serum components which do not bind to the fusion protein. The specific antibodies which bind to the inclusion bodies can then be eluted using conditions well-known in the art, and these antibodies can be separated from the inclusion bodies by again pelleting the inclusion bodies and removing the released antibodies. The small amount of fusion protein which is soluble then can be removed by brief contact with hydrophobic resins known to the art.

Conversely, the fusion protein can be linked to a solid support and the solid support can be incubated with the crude antibody to allow capture of the specific antibodies which bind to the fusion protein. These antibodies again can be released from the support using elution techniques well-known in the art.

The purified antibodies then can be coupled to a solid support to provide an affinity purification matrix capable of purification of the protein which contains the antigenic sequence encoded by the peptide used for immunization. This can be done by incubating a crude solution containing the target protein to the antibody bound on the resin, removing unbound materials by washing the solid support and then eluting the proteins which have specifically bound to the resin.

In such an application, if the ligand containing material is a protein, it is advantageous to retain the biological activity of the protein during the release of the protein from the resin. In such a case, some of the conditions which are used to release most antibodies from their ligands may be too harsh for the protein of interest to retain its bioactivity. Therefore, only that fraction of antibodies should be used for generation of the affinity resin that release under relatively mild conditions known as "soft release" conditions.

These can be isolated from the total antibody pool bound to the antigen by using the "soft release" conditions to dissociate the antibody from the fusion protein. This will ensure that the released antibody pool will contain primarily only those antibodies which dissociate from the antigen under mild conditions. Since such antibodies are normally isolated only after isolation of a monoclonal cell source which produces such an antibody, the current invention provides another advantage to the end user by simplifying the isolation of such antibodies from a polyclonal antibody pool.

Assay/Diagnostic Reagents

The present invention also is useful in the production of diagnostic reagents for use in diagnostic assays. The carrier protein conjugate, comprising the combination of carrier segment and ligand, can be adsorbed onto a variety of solid supports such as test tubes, microtiter plate wells, dipsticks, membranes and the like. Solid supports utilized in the assays are well-known to the art. Examples of solid supports can be found in U.S. Pat. No. 5,322,769 to Bolling et al. which is incorporated herein by reference for a description of the solid supports. Exemplary materials for such supports include hydrocarbon polymers such as polystyrene, polyethylene and polybutylene. Typically, the microtiter plates are coated with purified antigens or carrier protein conjugates. Alternatively, microtiter plates that previously have been coated with monoclonal antibodies specific for the carrier protein conjugates could be used to capture them.

The diagnostic reagents have a variety of uses. For example, a test sample suspected of having antibody to a particular analyte and a fluorescent enzyme or radiolabeled antibody is competitively reacted with the particular carrier protein conjugate on a solid support, and the amount of labeled antibody which binds to the particular antigen on the solid support is quantified. Particular carrier protein conjugates also are useful for agglutination reactions with antibodies. Other assays suitable for use with the carrier protein conjugates of the present invention are within the scope of those with knowledge in this particular art, some of which are described in the following paragraphs.

Types of Immunoassays

An ELISA process wherein the antibodies and/or carrier protein conjugates made by the process of the present invention used in combination with monoclonal antibodies, polyclonal antibodies, and soluble receptors also are contemplated. The advantage to this is that production and purification of carrier protein conjugates and subsequent antibodies are made much more quickly than under normal conditions.

KITS

The present invention also is directed to kits that utilize the process described. The kits are suitable for generating carrier protein conjugates and reliably making peptide/protein specific antibodies for use in a wide variety of techniques including protein purification, epitope mapping, detection by techniques such as Western Blotting, immunocytochemistry (ICC), immunoassays, and ELISA and for use in studies of protein/protein interactions.

A basic kit includes a container including the fusion protein carrier segment of the present invention which is a non-naturally occurring, hydrophobic, sparingly soluble amino acid sequence, and instructions for use.

Preferably, the nonantigenic fusion protein carrier segment is a non-naturally occurring, hydrophobic, sparingly soluble amino acid sequence having a length at least about 65 amino acids wherein the amino acid sequence lacks at least two of the following amino acids selected from the group consisting of the following negatively or positively charged side chains of amino acids: arginine, lysine, aspartic acid, glutamic acid; or uncharged side chains of the following amino acids: cysteine, tryptophan and methionine (with the exception of methionine at the amino terminal site).

Specifically, the fusion protein carrier segment is an amino acid sequence as illustrated in FIG. 1 [SEQ. ID. 1] or an amino acid sequence as illustrated in FIG. 3 [SEQ. ID. 2].

A second embodiment of the kit includes the vector encoding a carrier protein segment and instructions for its use. Such instructions may include those for the simple cloning, expression and purification of fusion proteins containing peptide antigens of choice in sufficient quantity for immunization of a host animal such as a chicken, mouse or rabbit, and for screening the resulting antibody pool. The customer clones in the DNA sequence corresponding to the peptide sequence of interest. Ideally, the produced fusion protein could be injected into animals without an adjuvant or second carrier protein to produce an antigenic response comparable to or better than that produced by current technologies. The amounts of the various reagents in the kits can be varied depending on a number of factors, such as the optimum sensitivity of the process.

The instructions for use are suitable to enable an end user to carry out the desired test. By the term "instructions for use," it is meant a tangible expression describing the reagent concentration for at least one assay method, parameters such as the relative amount of reagent and sample to be admixed, maintenance time periods for reagent/sample admixtures, temperature, buffer conditions and the like. It is within the scope of this invention to provide manual test kits or test kits for use in automated analyzers.

A third embodiment for the kit may be a method for detection of an antibody directed against a particular antigen. Such a kit typically includes the following items in amounts sufficient for at least one assay:

1. Solid support: a solid support having bound thereto one or more carrier protein conjugates that will specifically react with a desired antibody. Preferably the solid support is a preformed microtiter plate having the appropriate carrier protein conjugates bound to it.

2. Buffer to remove unbound proteins.

3. Solutions for detection of bound analyte

4. Instructions for use

A fourth embodiment for the kit is directed to a test kit for use in detecting the presence of proteins that bind a fusion protein in a test sample. The test kit consists of a container with a fusion protein, wherein the carrier segment comprises a non-naturally occurring, hydrophobic, sparingly soluble amino acid sequence and instructions. The antigen here, sometimes called an analyte, is the substance to be detected in a test sample. The antigen can be any substance for which there exists a naturally occurring, specific binding member such as an antibody. An analyte can be a substance that can bind to one or more specific members in an assay.

EXAMPLES

The following examples are presented to illustrate the advantages of the present invention and to assist one of ordinary skill in making and using the same. The examples are not intended in any way to otherwise limit the scope of the disclosure or protection granted by the patent.

Example 1

Creation of a Carrier Protein Segment From a Naturally Occurring Protein

The starting protein in question was gene 10 protein of phage T7- normally a protein of molecular weight about 35 kD. Test fusions of the intact gene 10 protein with the P50 test antigen [SEQ. ID. 4] were prepared and injected into rabbits. The antibodies produced by the rabbits overwhelmingly reacted with the gene 10 portion of the fusion protein and not with the test antigen. Since this construct (according to the method of Lin et al., 1987) failed the criteria for low antigenicity described herein, the sequence of a fragment of the gene 10 protein was redesigned as discussed below to obtain the desired properties. The details of the vector cloning are presented in Example 2. This example describes the design process that resulted in the selection of the amino acid sequence used.

As described below, the intent was to create as short a peptide sequence as possible which would be highly expressed and insoluble. A first attempt at creating a protein of 65 amino acids (carrier segment plus polylinker) was unsuccessful, but when 37 additional amino acids of designed sequence were added, expression was successful. The original sequence of the pGEMEX-1 amino acid sequence up to the site of the polylinker addition (Pvu2 site, FIG. 3 [SEQ. ID. 2]) is: ($H_2N$) - MASMTGGQQM GTNQGKGVVA AGDKLALFLK VFGGEVLTAF ARTSVTTSRH MVRSISSGKS AQFPVLGRTQ AAYLAPGEN-(COOH) [SEQ. ID. 6]

In designing the new sequence presented in FIG. 3, modifications were made as follows, which are in accordance with the design precepts in the Description of Invention section. Because the protein was already very hydrophobic, gross changes in amino acid hydrophobicity were not required:

| Site | Former Amino Acid | New Amino Acid(s) | Reason |
|---|---|---|---|
| 4 | M | V | eliminate met, conservative codon change |
| 10 | M | V | eliminate met, conservative codon change |
| 16 | K | H | eliminate lys, retain some charge at low pH |
| 23 | D | T | eliminate asp, half of unique Age1 site (cloning) |
| 24 | K | G | eliminate lys, half of unique Age1 site (cloning) |
| 30 | K | H | eliminate lys, retain some charge at low pH |
| 35 | E | T | eliminate glu |
| 42 | R | QH | eliminate arg, show that insertion into protein is tolerated |
| 49 | R | — | eliminate arg, show that deletion in protein is tolerated |
| 51 | M | V | eliminate tnet, conservative codon change |
| 53 | R | H | eliminate arg, retain some charge at low pH |
| 58 | G | A | remove gly from hydrophilic, possibly antigenic site |
| 59 | K | N | eliminate lys, conservative codon change |
| 68 | R | H | eliminate arg, retain some charge at low pH |
| 78 | E | N | eliminate glu, conservative codon change. |
| 79 | N | Q | creation of Pvu2 site (cloning) |

Example 2

Production of Proteins by Certain Vector Constructs
Creation of pMK 136 (clone consisting of AAs 1-41 and 79-102 of FIG. 3)

Two oligonucleotides of the following sequence were synthesized by standard means:
MK9
5'GGC TAG CTA GCG TGA CTG GTG GAC AGC AAG TGG GTA CTA ACC AAG GTC ACG GTG TAG TTG CTG CTG GAA CC 3'[SEQ. ID. 6]

MK10
5'GTC CGC TCG AGG TCG GAA TTC CCA GCT GAG CGA ACG CAG TCA GGA CGG TAC CGC CAA ATA CAT GCA AGA ACA ACG CCA GAC CGG T 3'[SEQ. ID. 7]

The oligonucleotides were designed so that they could be dimerized with Taq DNA polymerase using a "primer dimer reaction", using a 3 bp overlap of the 3' ends of the two oligonucleotides. The site of the overlap was designed to contain a unique Age1 site, so that integrity of the overlap in the dimer could be verified. The dimerization reaction was accomplished in the presence of 50 pmoles each oligonucleotide, 1 $\mu l$ Amplitaq DNA polymerase, standard buffer, Mg, and nucleotide levels, and 35 thermal cycles consisting of 30 seconds at 70° C. followed by 30 seconds of 95° C. The products of 15 standard 100 ul reactions were pooled and the dimer purified by electrophoresis on a 10% native polyacrylamide gel. The dimer DNA was passively eluted overnight, extracted with phenol, and ethanol precipitated. The ends of the dimerized oligos were trimmed with restriction enzymes Nhel and XhOl in standard buffers; the reaction was monitored by native PAGE gel.

PGEMEX-1 vector (Promega Corp, product #P2211) was cut with restriction enzymes Nhel and XhOl (monitored by agarose gel electrophoresis) and purified by phenol extraction and ethanol precipitation. The trimmed oligonucleotide dimers then were ligated into the cut vector with T4 DNA ligase, then the ligation products were used to transform bacterial strain BL21(DE3) plyss (a standard T7 expression strain, Novagen Corp, Madison, Wis., product #69451-2), using the protocol recommended by the manufacturer. The cells were plated onto LB-amp plates and grown overnight at 37° C. Colonies were picked into LB amp liquid culture, and plasmid was purified and analyzed for proper inserts by standard techniques. The DNA sequence across the area of interest for a plasmid from one positive clone, pMK136, was determined to be correct by standard techniques.

Expression of protein in the resultant strain was tested using conditions as described in the review article by Studier et al 1990. Reference also is made to U.S. Pat. No. 4,952,496 to Studier et al, which covers the use of T7 RNA polymerase in expression systems. The resultant clone was grown in LB—amp medium induced with 0.5 mM IPTG, and protein products analyzed by SDS-PAGE. No significant protein expression could be detected.

Thus, this first attempt at production of a vector encoding a carrier segment failed, possibly due to the short length of the encoded protein. The encoded protein in this case is 65 amino acids long; 41 amino acids before the Pvu2 site, and 24 amino acids encoded by the polylinker. The plasmid created in this section, pMK 136, was used as the starting point for the creation of the successful vector, pMK 149, and hence is included in this description.

Creation of pMK 144 (clone as depicted in FIG. 3)
Before cloning into pMK 136, a first step was to get rid of the plysS plasmid. This was accomplished by digesting a preparation of plasmid from pMK 136 with EcoRV, transforming into bacterial strain JM109 (Promega Corp., Madison, Wis.., Product #L2001), plating on LB-amp, and testing colonies for lack of resistance to chloramphenicol and resistance to ampicillin. A plasmid preparation was made from one such colony, and digested with Pvu2 under standard conditions (reaction monitored by agarose gel electrophoresis).

Two oligonucleotides of the following sequence were synthesized by standard means:
MK15

5'CT GGT TGC CCG GAG CCA GAT ACG CTG CCT GAG TAT GAC CCA GAA CAG GGA ACT GAG CGG AGT TAG CGC TGG AGA TGG AAT GTA CCA CGT GAG AAG TGG TCA CGG AGG TAT G 3'[SEQ. ID. 8]
MK16
5'CA TAC CTC CGT GAC CAC TTC TCA CGT GGT ACA TTC CAT CTC CAG CGC TAA CTC CGC TCA GTT CCC TGT TCT GGG TCA TAC TCA GGC AGC GTA TCT GGC TCC GGG CAA CCA G 3'[SEQ. ID. 9]

The two oligonucleotides were hybridized to each other by heating to 95° C. for 5 minutes followed by slow cooling to room temperature, then ligated into the cut vector with T4 DNA ligase, then the ligation products were used to transform bacterial strain BL21(DE3) plysS (a standard T7 expression strain, Novagen Corp, Madison, Wis., product #69451-2), using the protocol recommended by the manufacturer. The cells were plated onto LB-amp plates and grown overnight at 37° C. Colonies were picked into LB amp liquid culture, and plasmid was purified and analyzed for proper inserts by standard techniques. The DNA sequence across the area of interest for a plasmid from one positive clone, pMK144, was determined to be correct by standard techniques. A similar strain, pMK 149, was created in JM109 which lacked the plyss plasmid, by the aforementioned EcoRV digest technique. Plasmid from these cells was sequenced and used for all subsequent vector clonings.

Expression of protein in the pMK144 strain was tested using conditions as described in the review article by Studier et al (1990, supra.). The resultant clone was grown in LB—amp medium induced with 0.5 mM IPTG, and protein products analyzed by SDS-PAGE. As discussed in Example 2, expression from this strain was good, and serves as the carrier protein segment described in FIG. 3 and the preferred embodiment of the patent for a carrier segment/polylinker segment expression vector.

Creation of pMK 160 (insertion of p50 N-terminal epitopic peptide coding sequence into polylinker of pMK144)

A plasmid preparation was made from one such colony, and digested with Hind3 and Notl under standard conditions (reaction monitored by agarose gel electrophoresis).

Two oligonucleotides of the following sequence were synthesized by standard means; these encoded the synthesis of a 15-mer peptide sequence which is the N-terminal sequence of the eukaryotic transcription factor p50, with an additional lysine at the junction between the peptide and the carrier segment (usable to test cleavage with LysC), and an amber stop codon at the end of the peptide segment.
MK19
5'GG CCA AAA TGG CAG AAG ATG ATC CAT ATT TGG GAA GGC CTG AAC AAA TGT AG3'[SEQ. ID. 10]
MK20
5'AG CTC TAC ATT TGT TCA GGC CTT CCC AAA TAT GGA TCA TCT TCT GCC ATT TT 3'[SEQ. ID. 11]

The two oligonucleotides were hybridized to each other by heating to 95° C. for 5 minutes followed by slow cooling to room temperature, then ligated into the cut vector with T4 DNA ligase. The ligation products then were cut with Sphl under standard conditions to linearize any residual intact vector, then the ligation products were used to transform bacterial strain BL21(DE3) plyss (a standard T7 expression strain, Novagen Corp, Madison, Wis., product #69451-2), using the protocol recommended by the manufacturer. The cells were plated onto LB-amp plates and grown overnight at 37° C. Colonies were picked into LB amp liquid culture, and plasmid was purified and analyzed for proper inserts by standard techniques. The DNA sequence across the area of interest for a plasmid from one positive clone, pMK160, was determined to be correct by standard techniques.

Expression of protein in the pMK160 strain was tested using conditions as above.

Creation of pMK190-210:

These constructs, which were used in the expression and properties example below, were created by a cloning and expression strategy very similar to that used for pMK160. Specifically, two complementary oligonucleotides were created which coded for the peptide of interest and with ends compatible with in-frame cloning into the Notl-Hind3 site. The only extra feature of the oligos was that they were designed with 3 extra nucleotides at one end in order to create a new Nhel site at the Hind3 junction. This made screening for inserts easier, since digestion of an insert-containing plasmid with Nhel liberated a fragment of about 300 bp, whose size could accurately be determined by acrylamide gel electrophoresis. Otherwise, cloning and expression were as per standard protocol described above.

General Note About Comparing Vector-Encoded Proteins to Carrier Segment/Polylinker Definition in FIG. 3

The pMK144 expression strain and the pMK149 expression vector from which all fusion proteins used in the examples were derived, do not correspond exactly in encoded amino acid sequence to the carrier/polylinker segment of the fusion proteins. In the original vector, the first translation termination codon is encountered after amino acid leu102. In creating the fusion proteins used in the examples, for instance pMK160, the oligonucleotides encoding the peptide of interest were cloned into a Notl/Hind3 site, and contained a stop codon after the last amino acid of the desired peptide. This cloning strategy results in amino acids 95–102 of the sequence in FIG. 3 not being expressed in the fusion protein. Since amino acid 96 of FIG. 3 is a cysteine residue, if one wishes to couple a ligand to the carrier segment with a sulfhydrylreactive reagent, one can use the vector as is. Otherwise, it is advisable to insert a stop codon anywhere in the polylinker to avoid problems with the formation of disulfide bonds.

Expression and Purification of Carrier Segment-Containing Fusion Proteins 50 ml LB amp shake flasks were seeded with 1–5 ul of glycerol stock of each expression strain and grown at 37° C. overnight. In the morning, 30 ml of overnight culture was centrifuged for 5–10 minutes at 1,000–4,000×g at room temperature. The pellet from each culture was then transferred into 1 L cultures containing LB-amp prewarmed to 37° C., and incubated with shaking until an optical density at 600 nm of 0.5–1.0 was reached (about 3–4 hours after seeding). At that time, IPTG was added to 0.5 mM to induce expression, and cells were allowed to shake for 3–4 hours after induction. Samples could be taken for SDS-PAGE analysis as desired. After this time, cells were harvested by centrifugation at 3,000–5,000×g for >10 minutes. Cells then were processed directly, or stored for up to two weeks at −70° C. prior to use.

Cells were resuspended in 40 ml of buffer A (10 mM TrisHCl pH 8.0, 130 mM NaCl, 1 mM DTT), transferred to a 100 ml plastic beaker, chilled on ice water for 5 minutes, then sonicated (still in ice water batch) for 3 minutes with a Sonics and Materials VCX600 sonicator equipped with their standard macrotip, 0.5 seconds on, 0.5 seconds off, at a power setting of 55% (about 330 watts). Foaming was avoided to maximize cell breakage. After sonication, 4.5 ml of 20% sodium deoxycholate was added, and samples were again sonicated for 30 seconds. The lysates then were transferred to centrifuge tubes and spun at 15,000–20,000×G for 10 minutes at 4–10° C. (JA18 rotor). The supernatants were discarded, an optional second wash with 2% sodium Deoxycholate in buffer A was performed as desired, then the pellets were resuspended by brief sonication in isotonic phosphate buffered saline pH 7.4 containing 1 mM DTT and 1% Triton X-100. (Note: the Triton X-100 step may be omitted if desired to obtain material of slightly lesser purity and containing trace deoxycholate). The samples were pelleted as before, then washed at least 1× with isotonic phosphate buffered saline lacking excipients, then resuspended in 10 ml of the same buffer. Purified fusion proteins or carrier segment was then stored at −20° for as long as 6 months before use, if desired, and were ready for injection. In some cases, samples stored for long periods needed to be sonicated to reproduce a fine suspension before injection.

Expression Results

The protein was assayed as described in Example 3. The expression results are presented in part of Table 1, which follows this paragraph. Table 1 presents examples of proteins produced using the described invention and some properties thereof, including the amino acid sequence of the fused peptide, the size and charge of the fused peptide, the solubility in aqueous solution and retention time by reversed-phase HPLC, the optical density at which cells were induced and harvested, and the yield of purified fusion protein, in mg/liter. Table 1 indicates the strain number, the parent protein from which the peptide was selected, the number of amino acids in the attached peptide, the net charge of the attached peptide in neutral aqueous solutions, the optical density at which the cells were induced (harvested, if there is a second number), and the number of milligrams of fusion protein isolated from a liter of LB amp culture medium.

dard. 10 $\mu$l of sample was added to 200 $\mu$l reagent, then absorbances were read at 595 nm.

SDS-PAGE Analysis of purity: Samples of the fusion protein suspension were dissolved in 9 volumes of 4×Laemmli SDS gel loading buffer, heated to 95° C. for 5 minutes, then 20–40 $\mu$g of protein as estimated by the assay above were loaded onto Novex 4–20% SDS-PAGE gels (10 well combs). The running buffer contained 0.2–0.3% SDS instead of the usual 0.1%, in order to maintain the fusion protein in solution. After electrophoresis by manufacturer's standard conditions, the gels were stained with Coomassie Blue as per standard methods. The gel indicated a single major band with contaminant bands at less than 10% of total protein.

HPLC Analysis of purity and retention time: A sample was prepared as for the protein assay in acetic acid and analyzed by reversed phase high pressure liquid chromatography (HPLC). The stationary phase was a Vydac C-18 TP column, 10 $\mu$M silica, 4.6×250 mm dimensions. The mobile phase was standard (0.1% trifluoroacetic acid in water/acetonitrile), flow rate was 1 ml/minute, and detection was by UV absorbance at 214 nm, 0.3 AUFS. A 20 ul sample was injected, and eluted with a 40 minute linear gradient from 20%–60% acetonitrile. The results are depicted graphically in FIGS. 5A and 5B (HPLC) and numerically in Table 1 (supra). Retention times varied from 29.6 to 33.1 minutes (50–54% acetonitrile); quite late elution for proteins of this size thereby indicating their high hydrophobicity. Other than the large peak at the injection due to the acetic acid and small background peaks, which could be shown to be due to impurities in the acetic acid, the expressed protein eluted as a single sharp peak, in agreement with the SDS-PAGE results.

TABLE 1

| Bacterial Strain | Antigen Name | # of AA in Peptide | Net Charge | Sequence of the Insert (1 letter amino acid code) | SEQ. ID No. | Solubility (ug/ml) | HPLC Retention Time | O.D. | Yield (mg/L) |
|---|---|---|---|---|---|---|---|---|---|
| MK144 | base | 0 | 0 | none (for reference purposes) | n.a. | 0.81 | 33.1 | 0.7/1.23 | 11 |
| MK160 | p50 | 15 | −2 | KMAEDDPYLGRPEQM | 4 | 4.7 | 30.3 | 0.65/1.36 | 26 |
| MK189 | PIMT substrate | 13 | 1 | MKQVVNSAYEVIL | 12 | 1 | 31.2 | 1.1 | 14 |
| MK190 | AP2 | 19 | 3 | MSHTDNNAKSSDKEEKHRK | 13 | 2.3 | 29.6 | 1.2 | 6 |
| MK201 | SP1 | 19 | 3 | CKDSEGRGSGDPGKKKQHI | 14 | — | — | 0.558/1.15 | 19 |
| MK202 | Rantes | 17 | 0 | NPEKKWVREYINSLEMS | 15 | — | — | 0.52/0.95 | 37 |
| MK203 | MCAF | 21 | 2 | KQKNVQDSMDHLDKQTQTPKT | 16 | — | — | .809/1.3 | 31 |
| MK204 | IL2RG | 7 | 0 | YTLKPET | 17 | — | — | .727/1.32 | 33 |
| MK205 | TGFβ1 | 25 | 0 | YIYSLDTQYSKVLALNQHNPGASAA | 18 | — | — | .59/.9 | 30 |
| MK206 | EIF-2α | 10 | 2 | ILLSELSRRR | 19 | — | — | .878/2.22 | 71 |
| MK208 | PIMT | 19 | 1 | LMGVIYVPLTDKEKQWSWK | 20 | — | — | .35/.58 | 17 |
| MK209 | p49 | 19 | 3 | ETSSLLKIQTLAGHGGRRL | 21 | — | — | .843/1.7 | 36 |
| MK210 | SP1tail | 12 | −1 | MNSSSVPGDPPM | 22 | — | — | .505/1.25 | 36 |

There was little or no measurable expression of protein encoded by the plasmid in pMK136, as detected by SDS-PAGE or HPLC. Expression from the longer carrier segment vector pMK144 was substantial (11 mg/L), and expression of all the fusion proteins derived from it were above 5 mg/L culture (range 6–71 mg/liter, mean 27 mg/liter, standard deviation 16 mg/liter).

Example 3

Analysis of Purity and Properties of Carrier Segment and Fusion Proteins

Figure 5A:
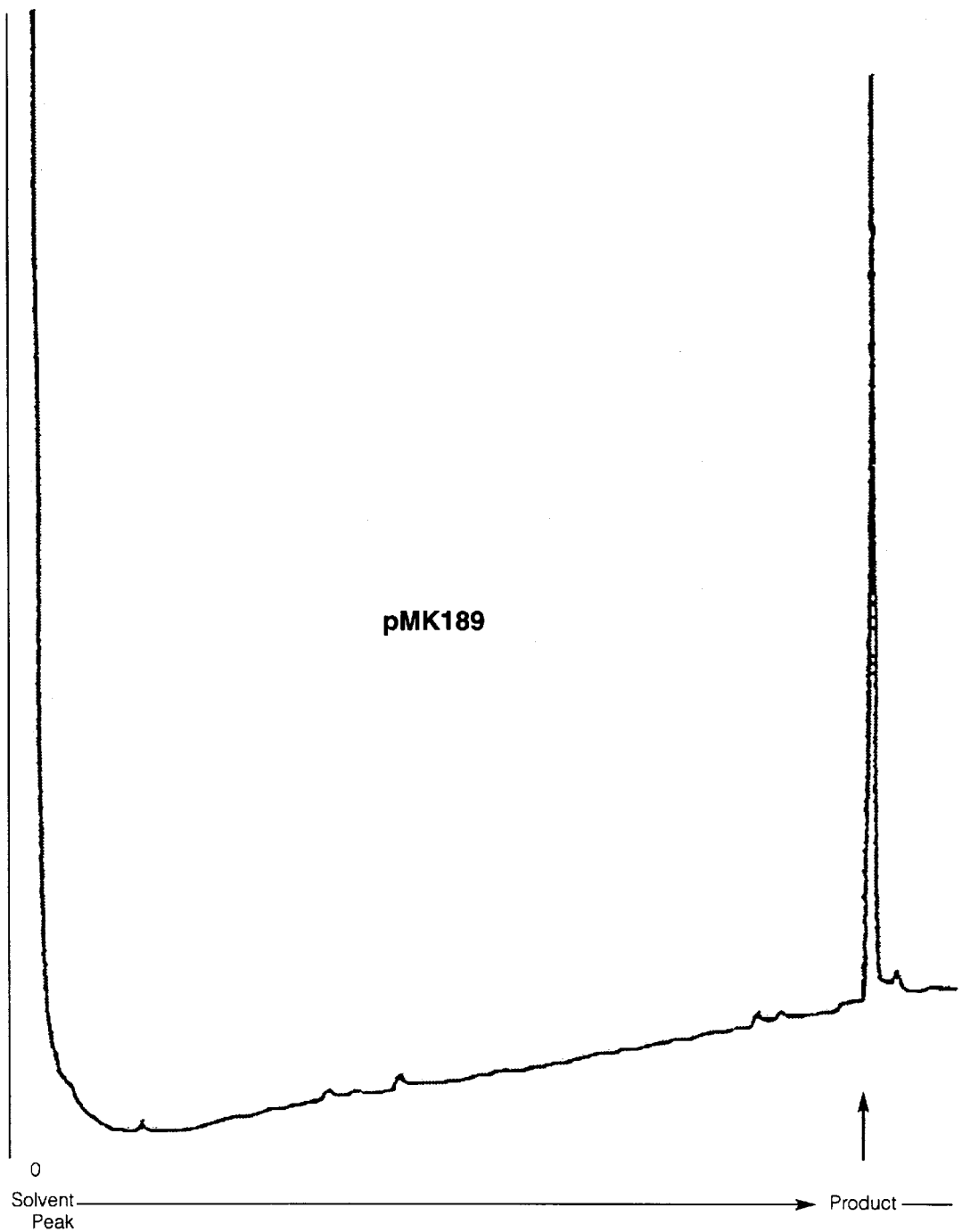
FIG. 5A is a graph illustrating purity assessments of fusion proteins purified by the method of the present invention as assessed by reversed-phase HPLC, and fast-atom bombardment mass spectrometry as described in Example 3.
Figure 5B:
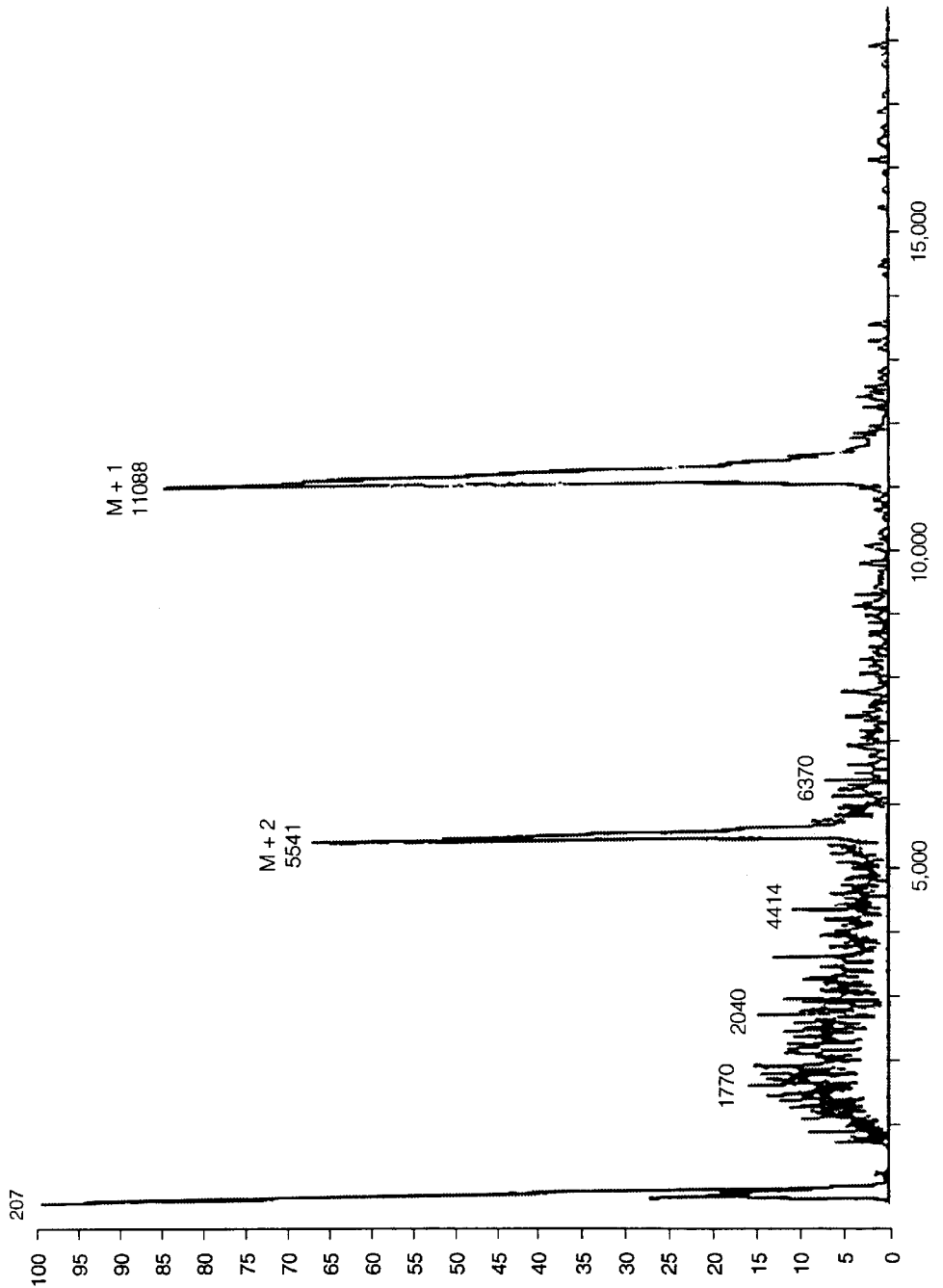
FIG. 5B is a graph illustrating purity assessments of fusion proteins purified by the method of the present invention as assessed by reversed-phase HPLC, and fast-atom bombardment mass spectrometry as described in Example 3.

Protein Assay: Samples of the fusion protein suspension were dissolved in an equal volume of glacial acetic acid, then diluted further 1:5 with 50% acetic acid. Diluted soluble samples then were assayed using Pierce Corp. Coomassie Plus Assay Reagent, using bovine serum albumin diluted in 50% acetic acid as a protein concentration stan- HPLC Analysis of Solubility: Samples of several fusions were allowed to stand in isotonic phosphate-buffered saline at 4° for several days with mixing until saturation was reached as estimated by the Protein Assay above. A protein standard was prepared by diluting an acetic acid-solubilized sample of protein from pMK160 until it was estimated to be about 100 $\mu$g/ml. This was aliquotted after confirmation of protein concentration by the protein assay above (final concentration 95 $\mu$g/ml). A serial 2-fold dilution series from 6 down to 0.75 $\mu$g/ml was assayed by HPLC as above, peak heights were measured, and a standard curve was plotted. Samples of saturated fusion proteins were diluted with an equal volume of glacial acetic acid, and assayed by HPLC relative to the pMK160 sample. Although the peak elution positions varied slightly from fusion to fusion, the peak shapes were very consistent, as can be seen in FIGS. 5A and 5B. The results, presented in Table 1, indicate that solubilities of the base protein (with extension as noted above) and fusions ranged from 0.8–4.7 μg/ml. The sizes of the peptide fusions tested ranged from 14–19 amino acids, and the net charge at neutral pH ranged from −3 to 3.

FAB-MS analysis of protein size: A purified sample of fusion protein purified from pMK160 was submitted to the Kratos Corporation (Ramsey, N.J.) for a demonstration run of their Kompact fast-atom bombardment mass spectrometer. As assayed by their standard methods and presented in FIG. 5B, the detected molecular weight of the major species (M+1) was 11,088 versus 11,086 as deduced from the sequence of the vector. The difference is within the error of the instrument.

Example 4
Immobilization of Carrier Protein Conjugates on Solid Surfaces

Figure 6:
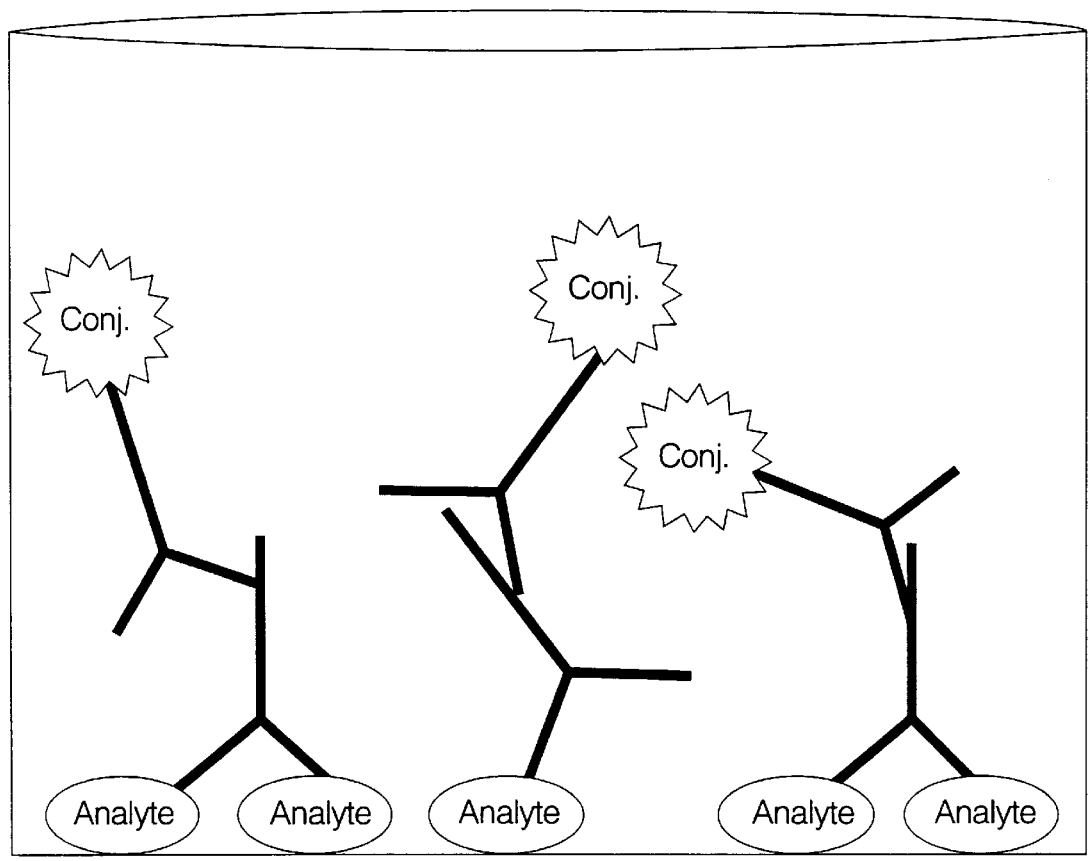
FIG. 6 is a diagram illustrating the immobilization of carrier protein conjugates on solid surfaces in Example 4.

An indirect ELISA (enzyme linked immunosorbent assay diagrammatically illustrated in FIG. 6) was performed by capitalizing on the capacity of carrier protein conjugates to be immobilized onto solid surfaces. Briefly, soluble carrier protein conjugate derived from the p50 protein sequence and suspended in phosphate buffered saline (PBS) was coated onto 96 well plates and incubated 14–18 hours at 4° C. The wells of the plates were washed four times with PBS containing 0.2% Tween 20 and then incubated 1 hour with a solution of 1% w/v bovine serum albumin to block nonspecific binding of proteins. The coated and blocked wells then were used to analyze immunoglobulin samples for specific antibody titers by incubating various concentrations of the sample for 1.5 hours at room temperature. The amount of specific antibody bound was detected using an anti-chicken antibody conjugate and developing the reaction with the appropriate substrate. The optical density of the calorimetric reaction directly correlates with the amount of specific antibody bound to the p50 carrier protein conjugate.

Figure 7:
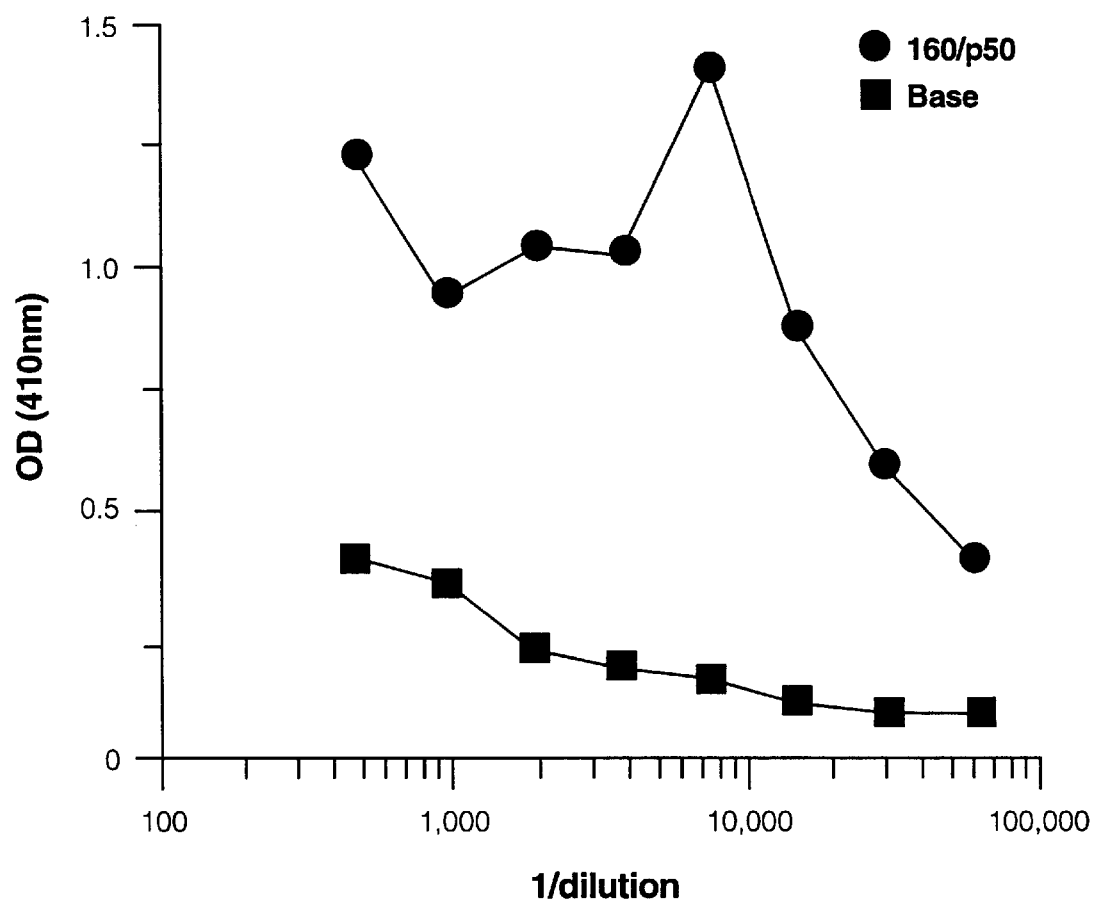
FIG. 7 is a graph illustrating the antigenic response of mice to a fusion protein made between the carrier protein of the present invention and a peptide segment derived from p50 and demonstrating the predominant antibody response is directed against the ligand, not the carrier segment, in Example 5.

Example 5
Injection of Proteins into Animals and Development of Antigenic Response by Animals Predominantly Directed Against the Ligand of Interest Female BALB/c mice (three per group) were immunized IP with 100 μg per injection of p50 carrier protein conjugate suspended in an equal volume (100 μl) of Complete Freund's Adjuvant. The mice were boosted twice at four week intervals with the same amount of immunogen in Incomplete Freund's Adjuvant. Two weeks after the last injection the mice were euthanized and the serum was collected. The specific antibody titers in the serum were assessed by indirect ELISA. Results from wells coated with the carrier protein (base) were compared to results from adjacent wells coated with the p50 carrier protein conjugate (160/p50). These results, shown in FIG. 7 as the mean OD per group per dilution, demonstrate that the vast majority of the specific antibody was preferentially directed against the peptide of interest.

Figure 8:
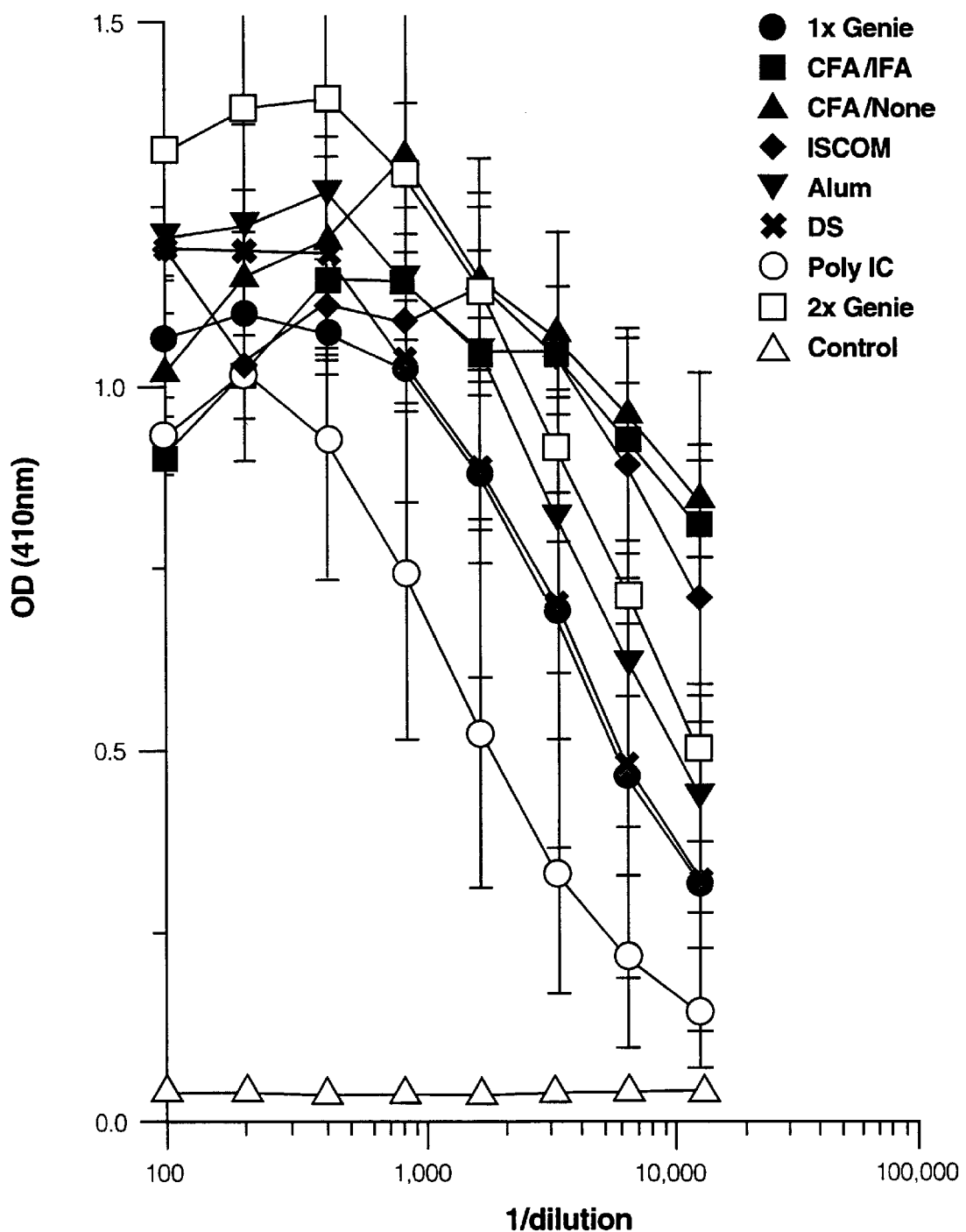
FIG. 8 is a graph illustrating the antibody titers from mice immunized with 1 mg/ml fusion peptide in the presence of Freund's adjuvant (complete at the primary and incomplete with each boost) and tested using different adjuvants in Example 6.

Example 6
Ability of System to Allow Antibodies to be Produced Without the Use of Adjuvant The antigenic response of mice to a fusion protein made between the carrier protein and a peptide segment derived from p50 was assessed with and without a variety of adjuvants. The experiment was conducted using the same injection regimen as was described in the preceding example. Six different adjuvants were used for comparison to injection with an equal amount (100 μg) of p50 carrier protein conjugate alone (1×Genie) and 200 μg of p50 carrier protein conjugate alone (2×Genie). The six different adjuvant groups consisted of Complete Freund's Adjuvant with the primary immunization followed by Incomplete Freund's Adjuvant at the boosts (CF/IF), Complete Freund's Adjuvant at the primary immunization and no adjuvant with the boosts (CF/none), a solution of 0.2 mg alum and 1 μg saponin per injection (ISCOM), 0.4 mg alum per injection (Alum), 2.5 mg dextran sulfate per injection (Dextran Sul) or 0.7 mg poly [I,C] per injection (Poly IC). Immunization with Freund's Adjuvant and no immunogen was used as the negative control (Control). In all cases, an equal volume of adjuvant (100 μl) was used with the immunogen. Injections without adjuvant (1×Genie and 2×Genie) also were normalized for volume using pyrogen-free saline solution. The serum titers of three mice per treatment group were assessed by indirect ELISA two weeks after the last boost. The results in FIG. 8 show that the specific antibody response of mice immunized with carrier peptide conjugate alone is comparable to that of mice injected with the immunogen suspended in adjuvant.

Example 7
Stimulation of Antigenic Response Over a Broad Antigen Dose Range

Example 7 is directed to the antigenic response of mice to various doses of a fusion protein made between the carrier protein and a peptide segment derived from p50.

Mice were injected with 100 μg antigen IP three times at four week intervals as previously described. Two weeks following the last injection, mice were euthanized and serum collected. Serum titers of antibody against the p50 carrier protein conjugate were assessed by indirect ELISA.

Figure 9A:
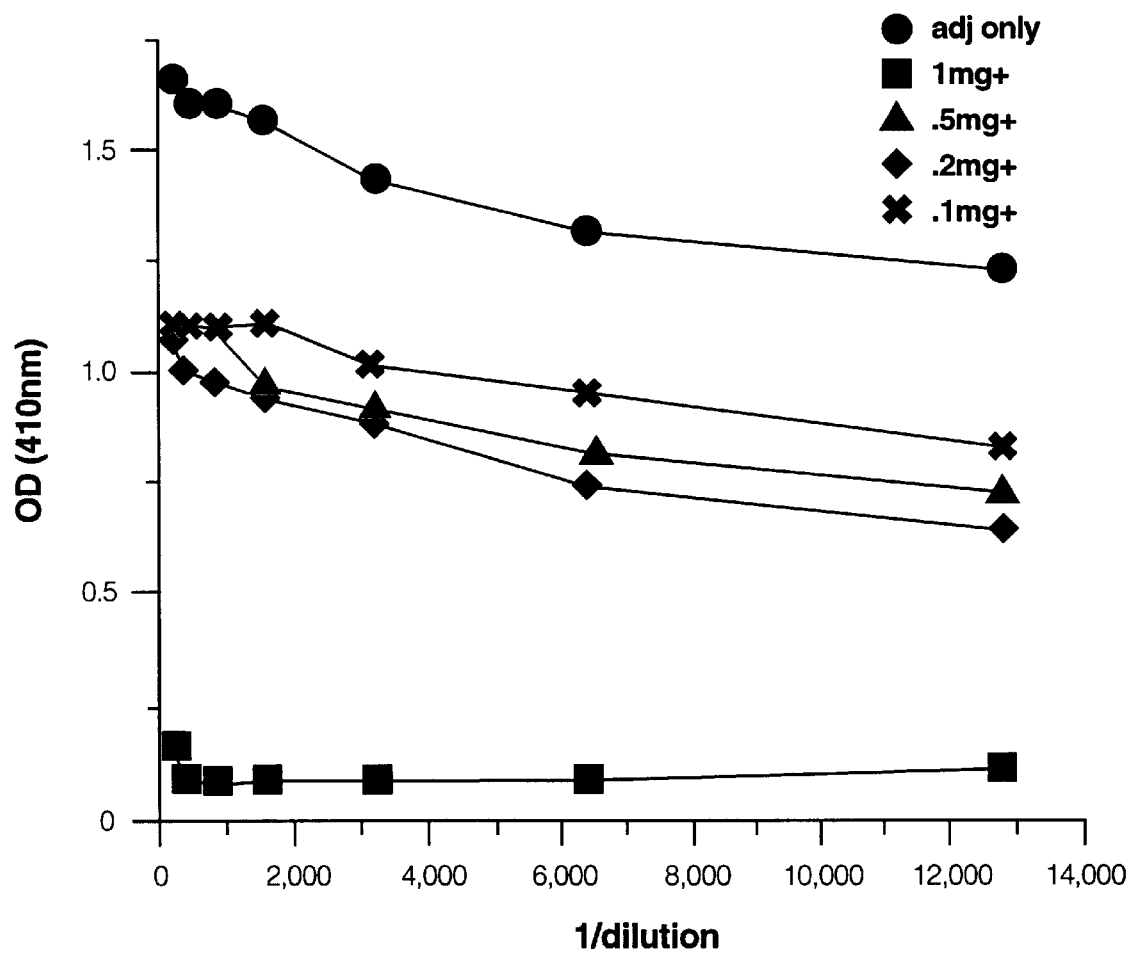
FIG. 9A is a graph illustrating the antibody titers from mice immunized with 2 mg/ml–0.1 mg/ml fusion peptide in the presence of adjuvant in Example 7.
Figure 9B:
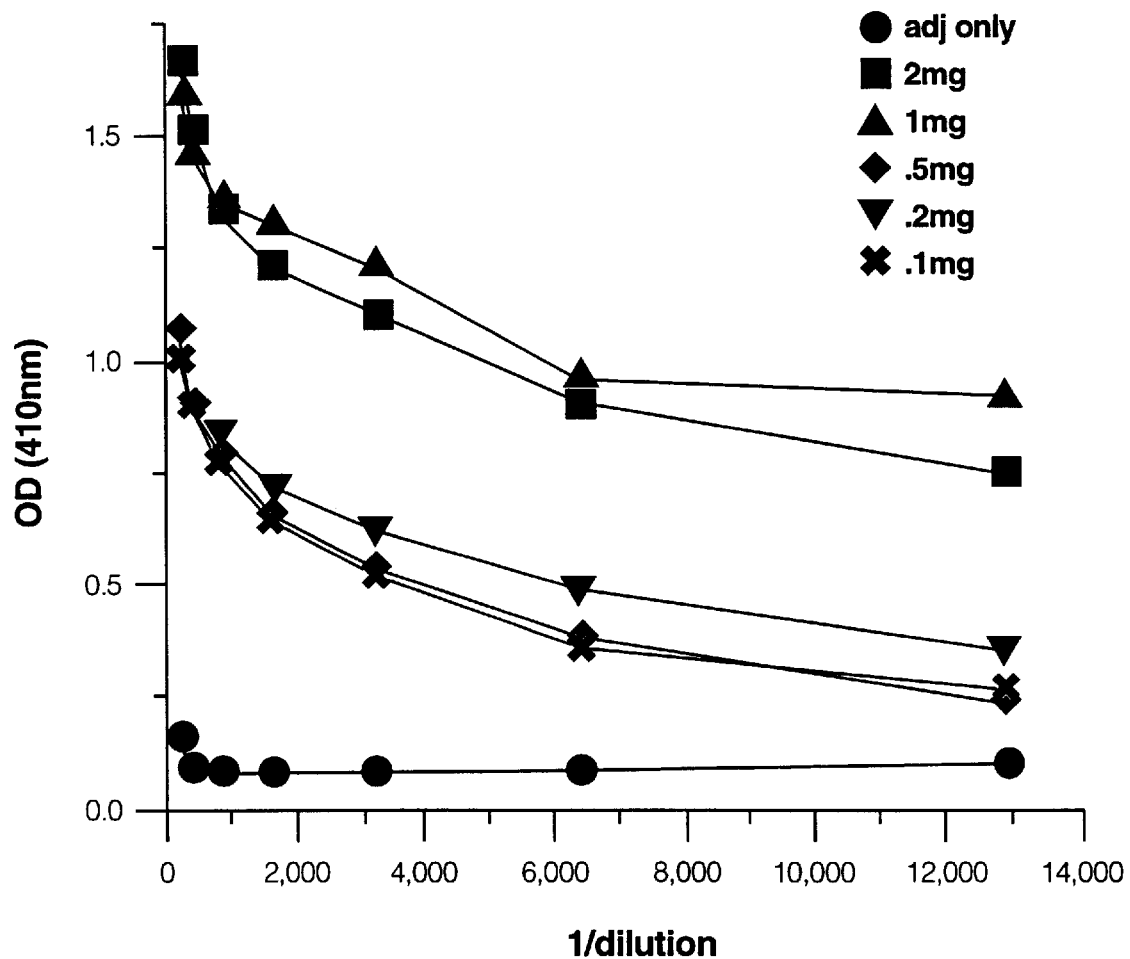
FIG. 9B is a graph illustrating the antibody titers from mice immunized with 2 mg/ml–0.1 mg/ml fusion peptide in the absence of adjuvant in Example 7.

The results are expressed as the mean $OD_{410}$ of sera from three BALB/c mice per treatment group. FIG. 9A illustrates the antibody titers from mice immunized with 100 μg–10 μg (1 mg/ml–0.1 mg/ml respectively), p50 carrier protein conjugate suspended in Freund's adjuvant (complete at the primary and incomplete with each boost). FIG. 9B illustrates the antibody titers from mice immunized with 200 μg–10 μg (2 mg/ml–0.1 mg/ml respectively), fusion peptide in the absence of adjuvant. These results demonstrate that the carrier protein conjugate is capable of stimulating a robust immune response of a wide range of doses with and without adjuvant. Mice immunized with adjuvant only (adj. only) were used as the negative control.

Figure 10:
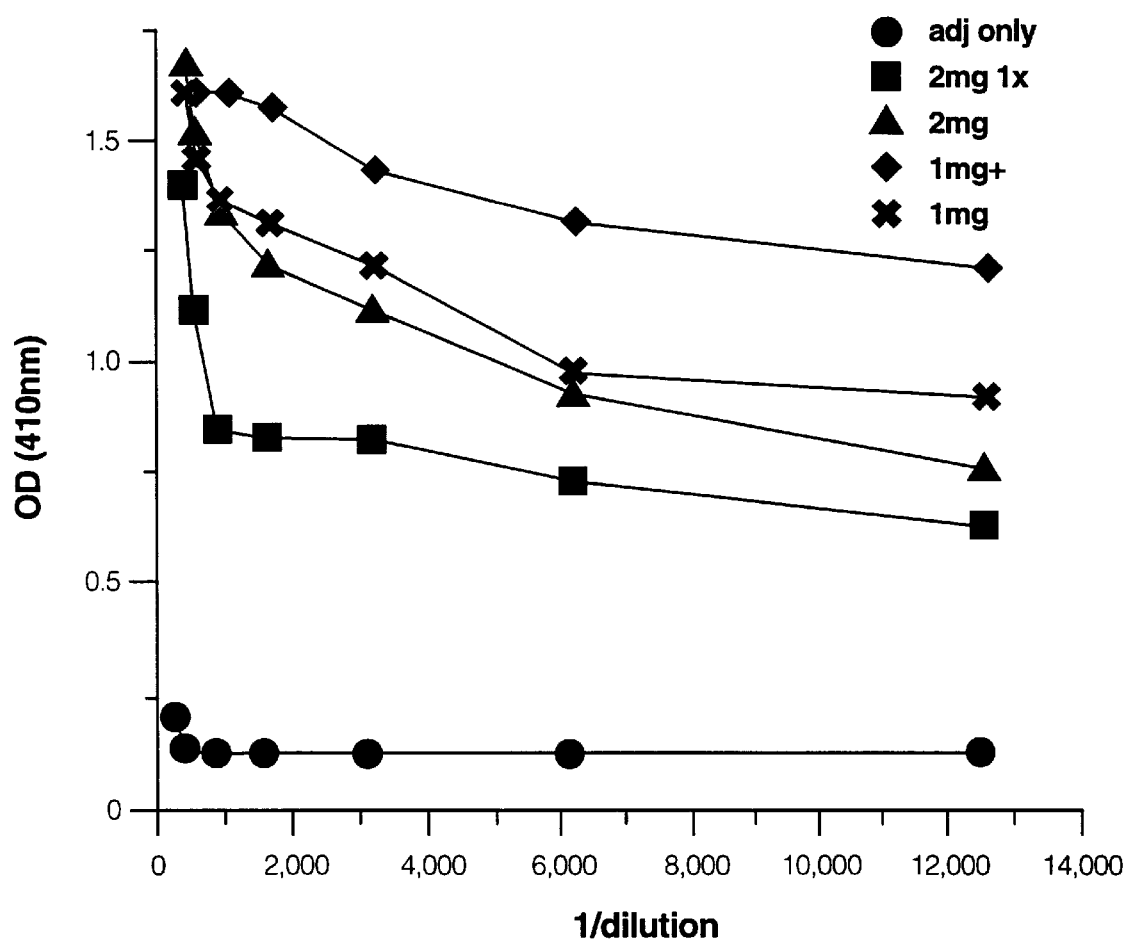
FIG. 10 is a graph illustrating the capacity of the system of the present invention to induce significant antibody response with a single injection as described in Example 8.

Example 8
Ability of System to Induce Significant Antibody Response with a Single Injection Female BALB/c mice were immunized IP with a single 200 μg (2 mg 1×) injection of a fusion protein made between the carrier protein and a peptide segment derived from p50. For comparison, age and gender-matched BALB/c mice were immunized with three IP injections of 100 μg p50 protein carrier conjugate in Freund's adjuvant (1 mg +) or 200 μg (2 mg) or 100 μg (1 mg) immunogen without adjuvant, all as previously described. Mice injected with adjuvant only (adj. only) were used as the negative control. Ten weeks following the primary immunization, mice were euthanized and serum collected. Serum antibody titers against the p50 carrier protein conjugate were assessed by indirect ELISA. The results are expressed as the mean $OD_{450}$ of serum from three mice per treatment group. As illustrated in FIG. 10, mice that received a single injection at the initiation of the study had a significant specific antibody response ten weeks later. The titers were comparable to those of other mice that had received multiple boosts with or without adjuvant.

Example 9
Production of Polyclonal Antibodies Using the System of the Present Invention with Immunization of Various Vertebrate Species and Routes of Immunization To demonstrate the versatility of the system, mice, rabbits and chickens were immunized with the p50 carrier protein conjugate of the present invention in Freund's adjuvant.

Female BALB/c mice and female New Zealand white rabbits were immunized with three injections, separated by three week intervals, via IP and SC routes, respectively. Two weeks following the last injection, the animals were euthanized and serum collected. White Leghorn laying hens were immunized by four weekly IM injections. Eggs were collected one week after the last injection for the isolation of antibody from the yolk.

Figure 11A:
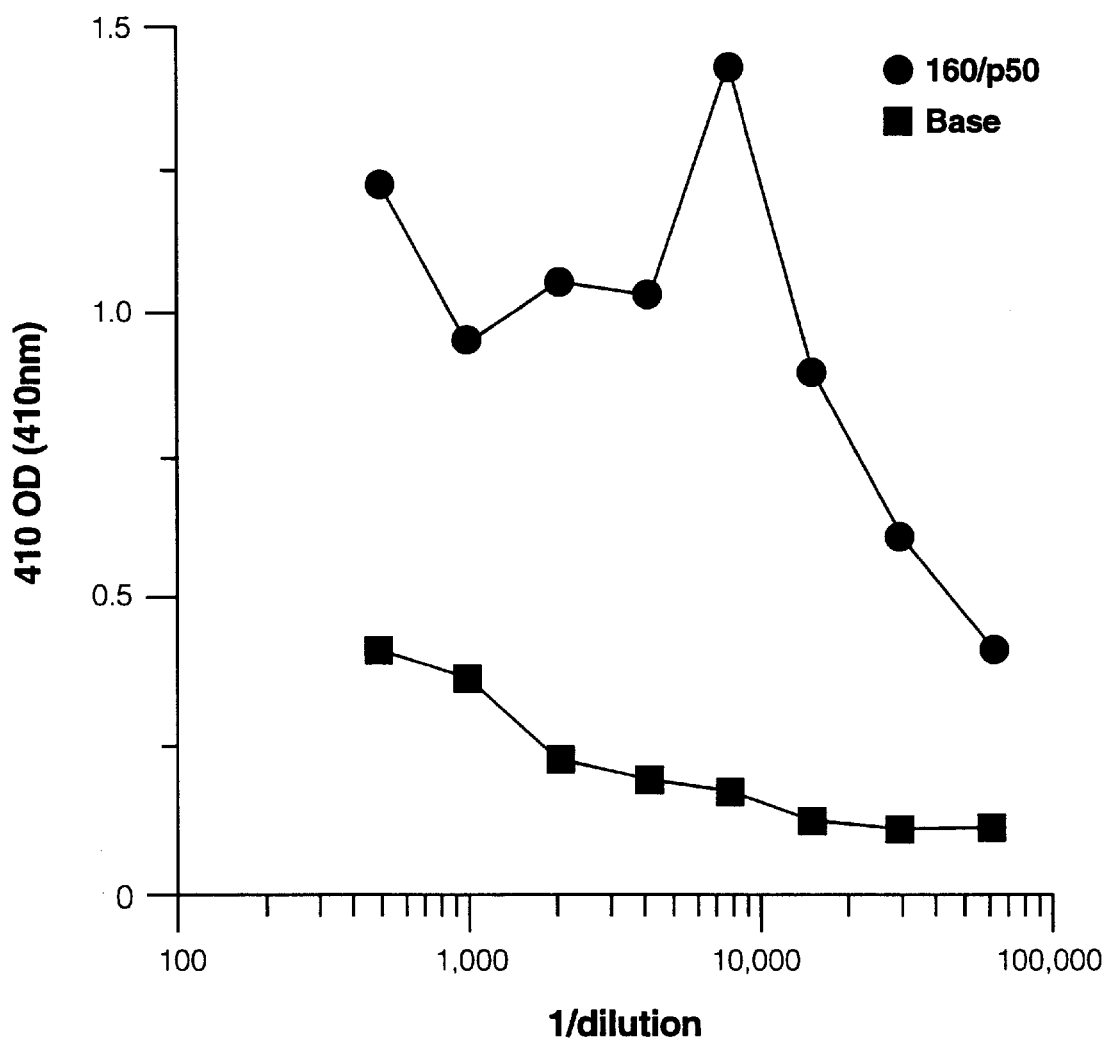
FIG. 11A is a graph illustrating the production of polyclonal antibodies in mice using the system of the present invention with immunization of mice in Example 9.
Figure 11B:
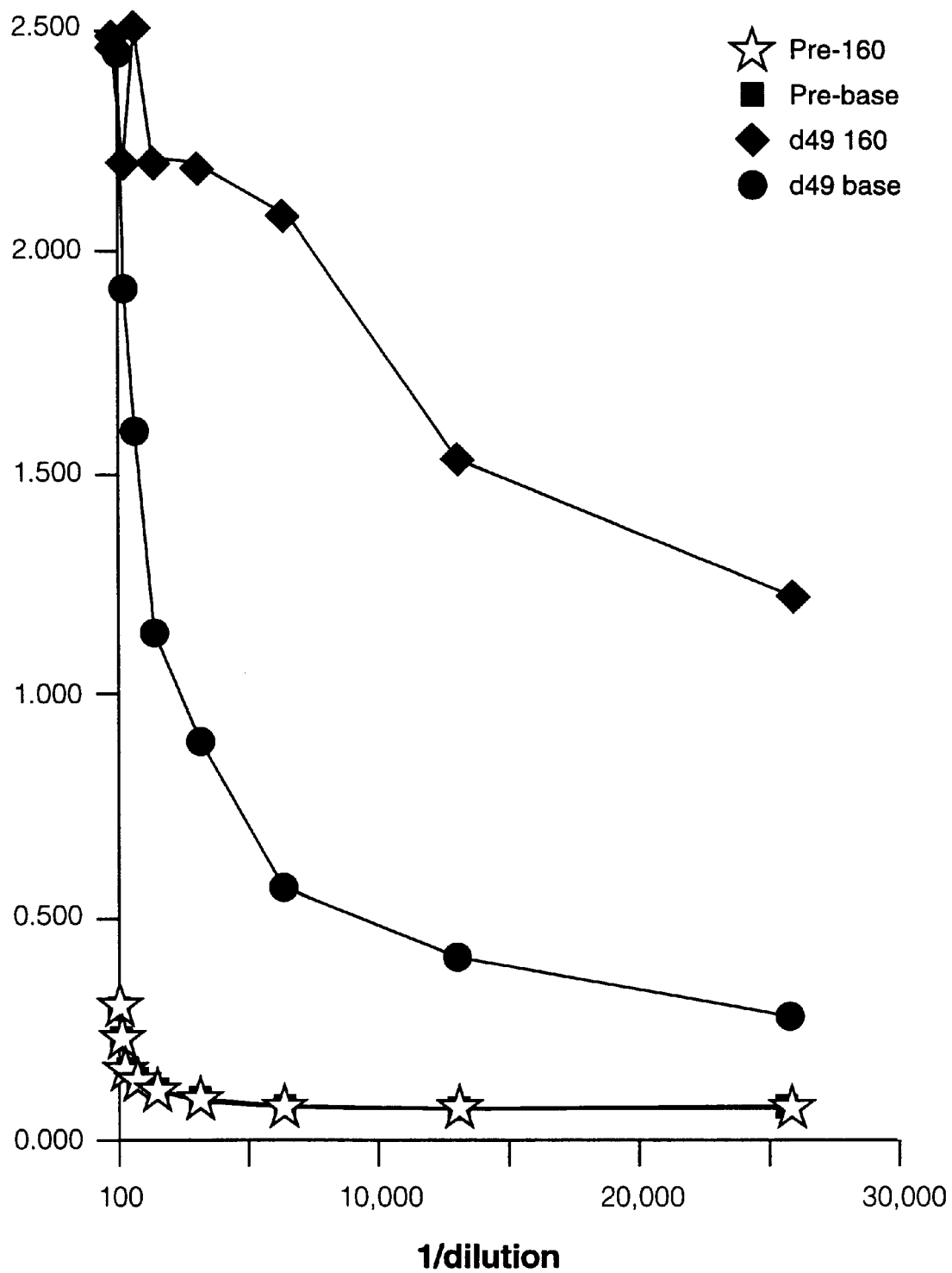
FIG. 11B is a graph illustrating the production of polyclonal antibodies in rabbits using the system of the present invention with immunization of mice in Example 9.
Figure 11C:
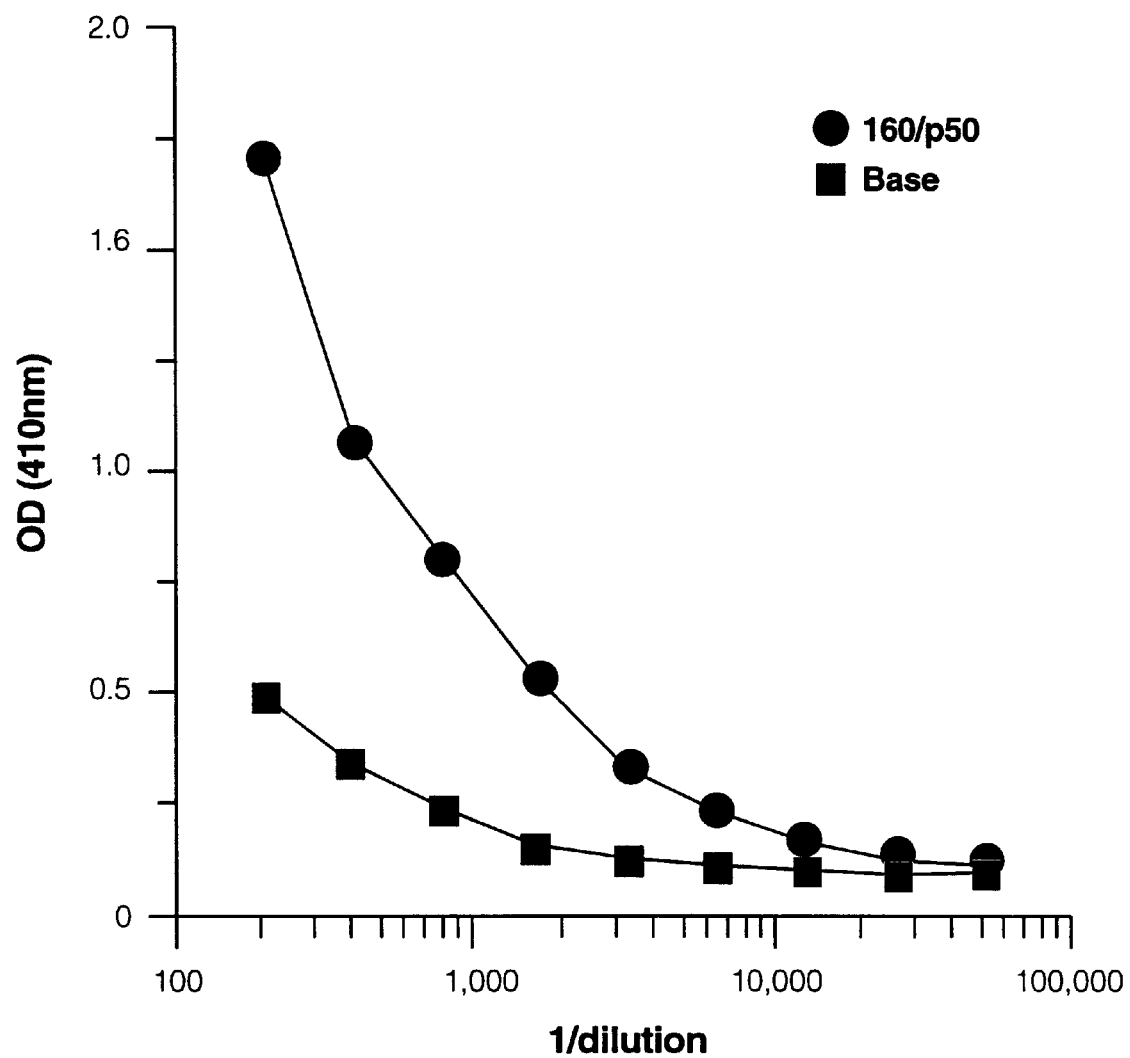
FIG. 11C is a graph illustrating the production of polyclonal antibodies in chickens using the system of the present invention with immunization of mice in Example 9.

The specific antibody titers of the animals to the p50 carrier protein conjugate and to the carrier (base) segment were determined by indirect ELISA as described in Example 4. FIG. 11A illustrates the mean titers of separate determinations showing high specific antibody titers to the peptide of interest in the serum of mice immunized by an IP route of injection. The specific antibody response of rabbits immunized via SC injections with the same p50 carrier protein conjugate is shown in FIG. 11B. Similarly, a high titer was achieved against the ligand of interest. Likewise, the specific antibody response of chickens immunized IM with p50 carrier protein conjugate is predominantly directed against the ligand portion of the molecule (FIG. 11C). Taken together, these data demonstrate the utility of this system in various vertebrate animal species- using different routes of injection.

Figure 12:
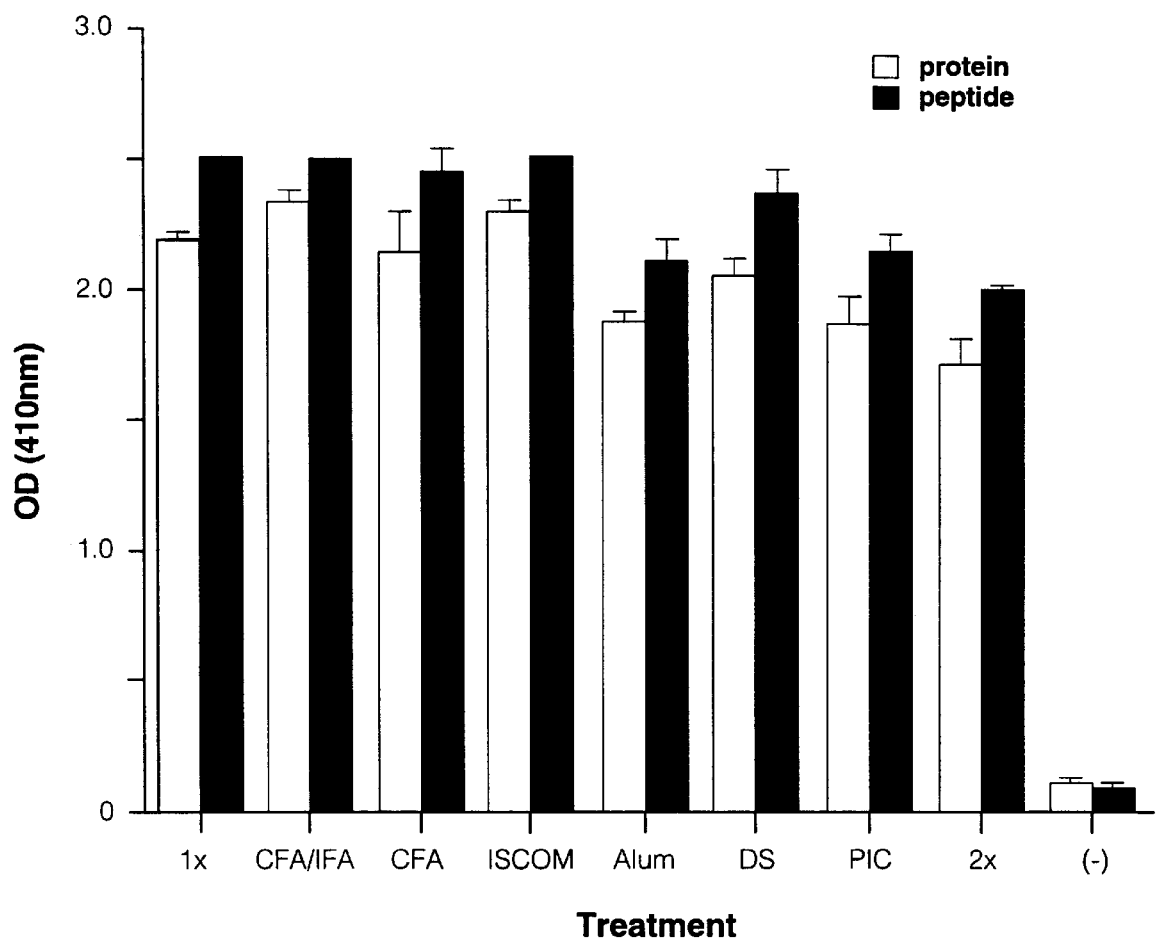
FIG. 12 is a graph illustrating the capacity of polyclonal antibodies made using the system of the present invention to bind peptides and full length target proteins in Example 10.

Example 10
Production of Polyclonal Antibodies Using This System Which Recognizes Both the Ligand Used For Immunogen and the Full Length Protein from Which the Ligand Was Derived Another important use of the present invention is to generate antibodies that will bind to the full length protein from which the peptide ligand was derived. To verify this use, antibodies were generated in mice using the p50 carrier protein conjugate with and without various exogenous adjuvants as described in Example 6. Specific antibody from the sera of these mice was evaluated by indirect ELISA, as previously described, comparing binding of antibody to p50 carrier protein conjugate to that of the full length p50 protein coated onto adjacent wells. As illustrated in FIG. 12, binding of specific antibody to the p50 carrier protein conjugate (peptide) was comparable to that of the p50 protein (Protein). Indeed the slight enhancement in binding to the full length protein was likely due to a small portion of the specific antibodies binding to the carrier portion of the carrier protein conjugate. The results are expressed as the mean ±SD $OD_{410}$ of three mice per treatment group.

Example 11
Production of High Proportions of Peptide-Specific Polyclonal Antibodies and Peptide-Specific Soft-Release Polyclonal Antibodies White Leghorn hens (chickens) were immunized with four weekly IM injections of a carrier protein conjugate derived from the gamma common chain protein with Freund's adjuvant as previously described. Eggs were collected several weeks after the last immunization and IgY antibody was purified from the yolks by sequential precipitation (IgY fx). Specific antibody was purified by affinity chromatography of the IgY fraction using the immunogen linked to an agarose resin. Soft release antibody was eluted with 2 M MgCl, pH 6.9 (soft release), whereas total specific antibody was eluted using 3 M MgCl, pH 3.0 (hard release). Specific antibody titers were assessed by indirect ELISA.

Figure 13:
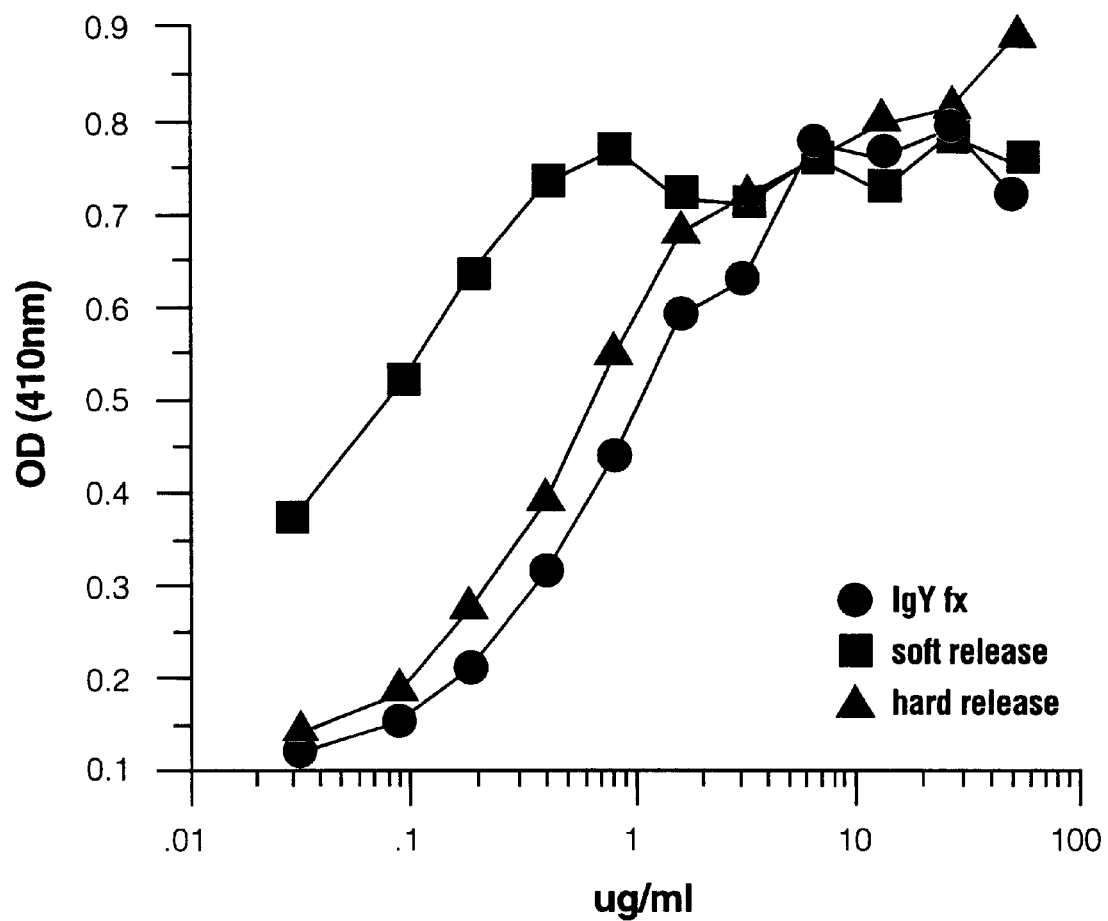
FIG. 13 is a graph illustrating the production of high proportions of peptide-specific polyclonal antibodies and peptide-specific, soft-release polyclonal antibodies in Example 11.

Reference is made to FIG. 13 for the results. The results demonstrate 7.6% total specific antibody (soft- and hard-release) and 1.5% specific soft-release antibody.

Example 12
Mitogenic Capacity of Fusion Peptide for Murine Splenocyte

Spleens of unimmunized female BALB/c mice were removed and monodispersed using frosted glass slides. Cells were resuspended at $10^6$ c/ml in RPMI 1640 containing 10% fetal bovine serum (FBS). Cell suspensions were incubated in 96 well flat-bottom plates (100 µl/well) and incubated for 72 hours at 37° C., 5% $CO_2$ in medium alone (none) or medium containing 5 µg/ml Con A, 10 µg/ml PHA, 5 µg/ml LPS or 5 µg/ml p50 carrier protein conjugate. Cellular proliferation was assessed following 72 hour incubation by LDH quantitation following cell lysis with a detergent solution.

Figure 14:
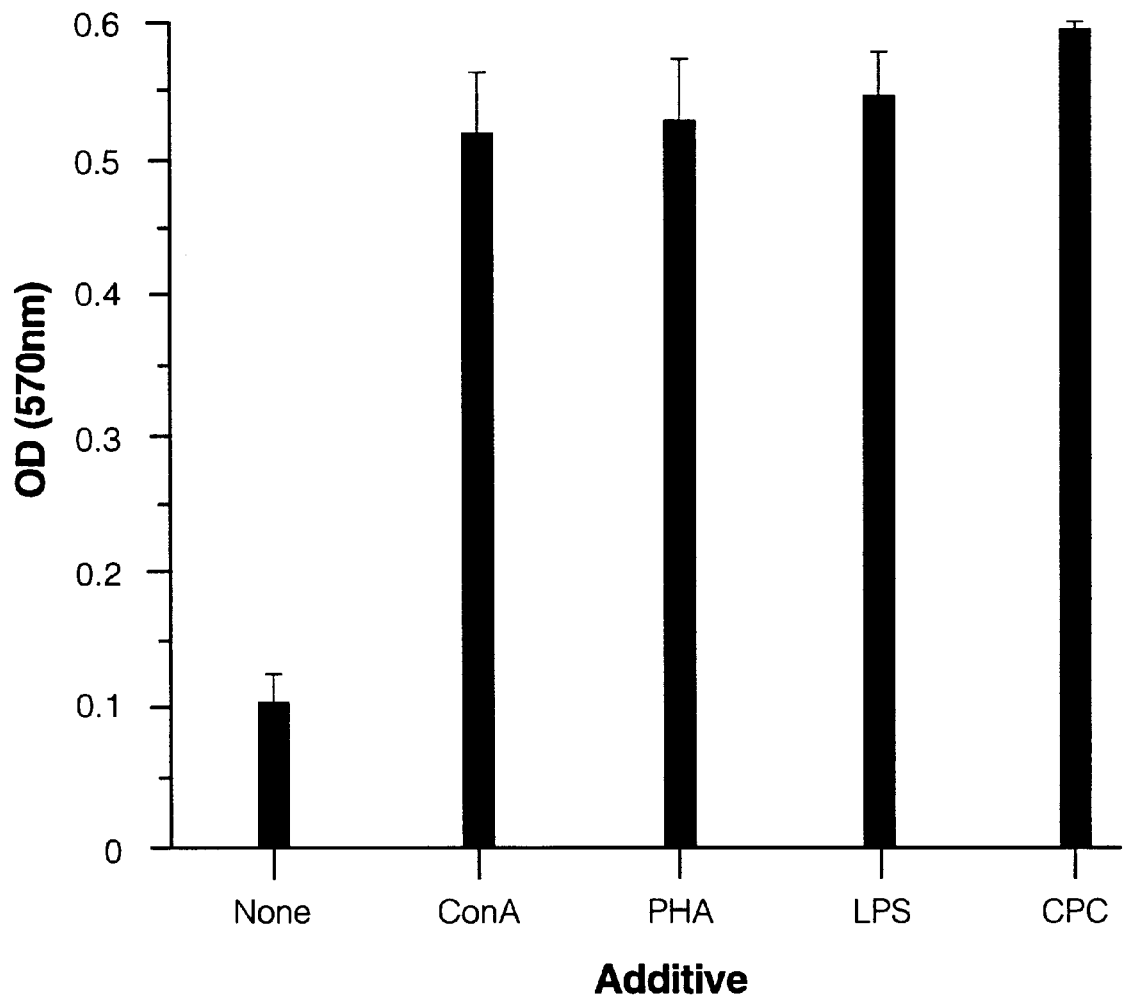
FIG. 14 is a graph illustrating the proliferative effects of the carrier segment on splenocytes from nonimmunized mice in Example 12.

Reference is made to FIG. 14 for the results of this experiment, which demonstrates that the proliferative response to the carrier protein conjugate (CPG) is comparable to that in response to ConA, PHA and LPS in spleen cells from unimmunized mice. This suggests the inherent mitogenic activity of the carrier protein conjugate. The results are expressed as the mean ±SD of three mice per treatment group. Assays were performed in triplicate.

Example 13
Isotype Varies with Immunogen Concentration in the Absence of Adjuvant To determine the influence of antigen dose on resulting antibody isotype, BALB/c mice were immunized 3 time IP with 0.2 ml p50 fusion protein in pyrogen-free phosphate buffered saline (no adjuvant) at 3 week intervals. Two weeks following the last injection, the mice were bled and euthanized. The predominant serum antibody isotypes were determined using the SangStat® isotyping kit and confirmed by indirect ELISA. Reference is made to Table 2 for the results, which are expressed as the rank order of predominant isotypes of 3 to 6 mice per treatment group.

TABLE 2

Immunogen Concentration Effects on Isotype Selection

| Concentration (mg/ml) | Isotype |
| --- | --- |
| 2 | IgG1 |
| 1 | IgG2b/1 |
| 0.5 | IgG2a/1 |
| 0.2 | IgG3/2a |
| 0.1 | IgG2a/2b |

The results indicate that immunization with high amounts of antigen yields predominantly $IgG_1$ antibody whereas low amounts typically yield predominantly IgG2a and IgG2b antibodies.

It is understood that the invention is not confined to the particular construction and arrangements herein illustrated and described, but embraces such modified forms thereof and come within the scope of the claims following the bibliography.

BIBLIOGRAPHY

U.S. Pat. No. 5,322,769 to Bolling et al.
U.S. Pat. No. 4,743,679 to Cohen et al.

U.S. Pat. No. 4,512,922 to Jones et al.
U.S. Pat. No. 5,302,526 to Keck et al.
U.S. Pat. No. 4,952,496 to Studier et al.
U.S. Pat. No. 5,322,930 to Tarnowski et al.
U.S. Pat. No. 5,008,373 to Kingsman et al.
Bolivar et al, 1977, *Gene* 2:95.
Clewell, D. R. et al, 1969, *Proc Nat Acad Sci USA* 62: 1159.
Cohen, S. N., 1972, *Proc Nat Acad Sci USA* 69: 2110.
*Current Protocols in Molecular Biology* (1994; chapter 16).

Klein, J., 1990 *Immunology*, Blackwell Scientific Publications, Inc. Massachusetts, 269–293.
Kohler & Milstein, 1976, *Nature*, 296: 495.
Lin, S. et al., 1987, *Biochemistry*, 26: 5267–5274.
Maniatis et al., 1989, *Molecular Cloning; A Laboratory Manual*, 2d. Ed. :254
Santo, C. et al., 1992, *Science* 258: 120–122.
Smith, A. J. et al., 1992, *Techniques in Protein Chemistry III*, 219–229.
Studier F. W., et al, 1990, *Meth. Enzym.* 185: 60–89.
Tae H. J., et al., 1983, *Methods in Enzymology* (Chapter 51), Academic Press, Inc., 91: 580–609.

What is claimed is:

1. A process for producing an antibody to a ligand, comprising:
   a. providing a fusion protein carrier segment having the following characteristics:
      has a non-naturally occurring amino acid sequence having a length of about 65 to about 100 amino acids, at least 95% of the amino acid sequence consisting of amino acids selected from the group consisting of glycine, alanine, valine, leucine, isoleucine, serine, threonine, proline, glutamine, asparagine, phenylalanine, tyrosine, and histidine;
      is hydrophobic; and
      has low solubility as determined by detection in an inclusion body fraction resulting when cells expressing a fusion protein are lysed and treated by washing with neutral aqueous solutions containing nonionic detergents, wherein the fusion protein consists of the carrier segment fused to a peptide ligand;
   b. providing a ligand;
   c. fusing the fusion protein carrier segment to the ligand to form a carrier protein conjugate;
   d. producing an antibody to the ligand by presenting the carrier protein conjugate to a system.

2. The process of claim 1, wherein the antibody is produced by an in vivo process after injecting the carrier protein conjugate into a host animal.

3. The process of claim 1, wherein the antibody is produced by an in vitro process of incubating the carrier protein conjugate with in vitro cultured cells.

4. A process according to claim 1 wherein the fusion protein carrier segment is further characterized by low antigenically wherein low antigenicity is defined as failure of the carrier segment to induce formation of greater than 50% of all specific antibodies generated in response to at least three injections into a host animal of a fusion protein consisting of the carrier segment fused to a peptide ligand, said peptize ligand to determine antigenicity having the sequence: H$_2$N-Lys Met Ala Glu Asp Asp Pro Tyr Leu Gly Arg Pro Glu Gin Met.

5. A process according to claim 1 wherein the ligand provided does nor require use of an adjuvant to elicit an immune response to the ligand when the ligand is fused to the fusion protein carrier segment.

* * * * *

UNITED STATES PATENT AND TRADEMARK OFFICE
CERTIFICATE OF CORRECTION

PATENT NO. : 5,989,554
DATED : November 23, 1999
INVENTOR(S) : Knuth et al.

It is certified that error appears in the above-identified patent and that said Letters Patent is hereby corrected as shown below:

Column 50, claim 4,
Line 45, "antigenically" should be -- antigenicity --.

Column 50, claim 5,
Line 53, "nor" should be -- not --.

Signed and Sealed this

Twelfth Day of March, 2002

Attest:

JAMES E. ROGAN
Attesting Officer
Director of the United States Patent and Trademark Office

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 79 amino acids
      (B) TYPE: amino acid
      (C) STRANDEDNESS: unknown
      (D) TOPOLOGY: linear (ii) MOLECULE TYPE: protein (xi) SEQUENCE DESCRIPTION: SEQ ID NO:1:

Met Ala Ser Val Thr Gly Gly Gln Gln Val Gly Thr Asn Gln Gly His
1               5                   10                  15

Gly Val Val Ala Ala Gly Thr Gly Leu Ala Leu Phe Leu His Val Phe
            20                  25                  30

Gly Gly Thr Val Leu Thr Ala Phe Ala Gln His Thr Ser Val Thr Thr
        35                  40                  45

Ser His Val Val His Ser Ile Ser Ser Ala Asn Ser Ala Gln Phe Pro
    50                  55                  60

Val Leu Gly His Thr Gln Ala Ala Tyr Leu Ala Pro Gly Asn Gln
65                  70                  75

(2) INFORMATION FOR SEQ ID NO:2:

(i) SEQUENCE CHARACTERISTICS:
      (A) LENGTH: 102 amino acids
      (B) TYPE: amino acid
      (C) STRANDEDNESS: unknown
      (D) TOPOLOGY: linear (ii) MOLECULE TYPE: protein (xi) SEQUENCE DESCRIPTION: SEQ ID NO:2:

Met Ala Ser Val Thr Gly Gly Gln Gln Val Gly Thr Asn Gln Gly His
1               5                   10                  15

Gly Val Val Ala Ala Gly Thr Gly Leu Ala Leu Phe Leu His Val Phe
            20                  25                  30

Gly Gly Thr Val Leu Thr Ala Phe Ala Gln His Thr Ser Val Thr Thr
        35                  40                  45

Ser His Val Val His Ser Ile Ser Ser Ala Asn Ser Ala Gln Phe Pro
    50                  55                  60

Val Leu Gly His Thr Gln Ala Ala Tyr Leu Ala Pro Gly Asn Gln Leu
65                  70                  75                  80

Gly Ile Pro Thr Ser Arg Asp Pro Gly Pro Leu Asp Ala Ala Ala Cys
                85                  90                  95

Ile Ser Leu Ser Ile Leu
            100

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:3:

Leu Gly Ile Pro Thr Ser Arg Asp Pro Gly Pro Leu Asp Ala Ala Ala
1               5                   10                  15

Cys Ile Ser Leu Ser Ile Leu
                20

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:4:

Lys Met Ala Glu Asp Asp Pro Tyr Leu Gly Arg Pro Glu Gln Met
1               5                   10                  15

(2) INFORMATION FOR SEQ ID NO:5:

(i) SEQUENCE CHARACTERISTICS:
        (A) LENGTH: 79 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:5:

Met Ala Ser Met Thr Gly Gly Gln Gln Met Gly Thr Asn Gln Gly Lys
1               5                   10                  15

Gly Val Val Ala Ala Gly Asp Lys Leu Ala Leu Phe Leu Lys Val Phe
                20                  25                  30

Gly Gly Glu Val Leu Thr Ala Phe Ala Arg Thr Ser Val Thr Thr Ser
            35                  40                  45

Arg His Met Val Arg Ser Ile Ser Ser Gly Lys Ser Ala Gln Phe Pro
        50                  55                  60

Val Leu Gly Arg Thr Gln Ala Ala Tyr Leu Ala Pro Gly Glu Asn
65                  70                  75

(2) INFORMATION FOR SEQ ID NO:6:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGCTAGCTAG CGTGACTGGT GGACAGCAAG TGGGTACTAA CCAAGGTCAC GGTGTAGTTG      60

CTGCTGGAAC C      71

(2) INFORMATION FOR SEQ ID NO:7:

(i) SEQUENCE CHARACTERISTICS:
      (A) LENGTH: 85 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:7:

GTCCGCTCGA GGTCGGAATT CCCAGCTGAG CGAACGCAGT CAGGACGGTA CCGCCAAATA      60

CATGCAAGAA CAACGCCAGA CCGGT      85

(2) INFORMATION FOR SEQ ID NO:8:

(i) SEQUENCE CHARACTERISTICS:
      (A) LENGTH: 111 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:8:

CTGGTTGCCC GGAGCCAGAT ACGCTGCCTG AGTATGACCC AGAACAGGGA ACTGAGCGGA      60

GTTAGCGCTG GAGATGGAAT GTACCACGTG AGAAGTGGTC ACGGAGGTAT G      111

(2) INFORMATION FOR SEQ ID NO:9:

(i) SEQUENCE CHARACTERISTICS:
      (A) LENGTH: 111 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:9:

CATACCTCCG TGACCACTTC TCACGTGGTA CATTCCATCT CCAGCGCTAA CTCCGCTCAG      60

TTCCCTGTTC TGGGTCATAC TCAGGCAGCG TATCTGGCTC CGGGCAACCA G      111

(2) INFORMATION FOR SEQ ID NO:10:

(i) SEQUENCE CHARACTERISTICS:
      (A) LENGTH: 52 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:10:

GGCCAAAATG GCAGAAGATG ATCCATATTT GGGAAGGCCT GAACAAATGT AG      52

(2) INFORMATION FOR SEQ ID NO:11:

(i) SEQUENCE CHARACTERISTICS:
      (A) LENGTH: 52 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:11:

AGCTCTACAT TGTTCAGGC CTTCCCAAAT ATGGATCATC TTCTGCCATT TT                52

(2) INFORMATION FOR SEQ ID NO:12:

(i) SEQUENCE CHARACTERISTICS:
                (A) LENGTH: 13 amino acids
                (B) TYPE: amino acid
                (C) STRANDEDNESS: unknown
                (D) TOPOLOGY: linear (ii) MOLECULE TYPE: protein (xi) SEQUENCE DESCRIPTION: SEQ ID NO:12:

Met Lys Gln Val Val Asn Ser Ala Tyr Glu Val Ile Leu
1               5                   10

(2) INFORMATION FOR SEQ ID NO:13:

(i) SEQUENCE CHARACTERISTICS:
                (A) LENGTH: 19 amino acids
                (B) TYPE: amino acid
                (C) STRANDEDNESS: unknown
                (D) TOPOLOGY: linear (ii) MOLECULE TYPE: protein (xi) SEQUENCE DESCRIPTION: SEQ ID NO:13:

Met Ser His Thr Asp Asn Asn Ala Lys Ser Ser Asp Lys Glu Glu Lys
1               5                   10                  15

His Arg Lys (2) INFORMATION FOR SEQ ID NO:14:

(i) SEQUENCE CHARACTERISTICS:
                (A) LENGTH: 19 amino acids
                (B) TYPE: amino acid
                (C) STRANDEDNESS: unknown
                (D) TOPOLOGY: linear (ii) MOLECULE TYPE: protein (xi) SEQUENCE DESCRIPTION: SEQ ID NO:14:

Cys Lys Asp Ser Glu Gly Arg Gly Ser Gly Asp Pro Gly Lys Lys Lys
1               5                   10                  15

Gln His Ile (2) INFORMATION FOR SEQ ID NO:15:

(i) SEQUENCE CHARACTERISTICS:
                (A) LENGTH: 17 amino acids
                (B) TYPE: amino acid
                (C) STRANDEDNESS: unknown
                (D) TOPOLOGY: linear (ii) MOLECULE TYPE: protein (xi) SEQUENCE DESCRIPTION: SEQ ID NO:15:

Asn Pro Glu Lys Lys Trp Val Arg Glu Tyr Ile Asn Ser Leu Glu Met
1               5                   10                  15

Ser (2) INFORMATION FOR SEQ ID NO:16:

(i) SEQUENCE CHARACTERISTICS:
    (A) LENGTH: 21 amino acids
    (B) TYPE: amino acid
    (C) STRANDEDNESS: unknown
    (D) TOPOLOGY: linear (ii) MOLECULE TYPE: protein (xi) SEQUENCE DESCRIPTION: SEQ ID NO:16:

```
Lys Gln Lys Asn Val Gln Asp Ser Met Asp His Leu Asp Lys Gln Thr
1               5                  10                  15

Gln Thr Pro Lys Thr
            20
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:17:

```
Tyr Thr Leu Lys Pro Glu Thr
1               5
```

(2) INFORMATION FOR SEQ ID NO:18:

(i) SEQUENCE CHARACTERISTICS:
        (A) LENGTH: 25 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:18:

```
Tyr Ile Tyr Ser Leu Asp Thr Gln Tyr Ser Lys Val Leu Ala Leu Asn
1               5                  10                  15

Gln His Asn Pro Gly Ala Ser Ala Ala
            20                  25
```

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:19:

```
Ile Leu Leu Ser Glu Leu Ser Arg Arg Arg
1               5                  10
```

(2) INFORMATION FOR SEQ ID NO:20:

(i) SEQUENCE CHARACTERISTICS:
        (A) LENGTH: 19 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:20:

```
Leu Met Gly Val Ile Tyr Val Pro Leu Thr Asp Lys Glu Lys Gln Trp
1               5                   10                  15

Ser Trp Lys (2) INFORMATION FOR SEQ ID NO:21:

(i) SEQUENCE CHARACTERISTICS:
        (A) LENGTH: 19 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:21:

Glu Thr Ser Ser Leu Leu Lys Ile Gln Thr Leu Ala Gly His Gly Gly
1               5                   10                  15

Arg Arg Leu (2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:22:

Met Asn Ser Ser Ser Val Pro Gly Asp Pro Pro Met
1               5                   10
```